United States Patent [19]

Fujiwa et al.

[11] Patent Number: 5,338,879
[45] Date of Patent: Aug. 16, 1994

[54] LACTONE-MODIFIED ALICYCLIC COMPOSITION AND AN EPOXIDIZED COMPOSITION THEREOF

[75] Inventors: Takaaki Fujiwa; Shin Takemoto, both of Otake; Tomohisa Isobe, Iwakuni; Yoshiyuki Harano, Otake, all of Japan

[73] Assignee: Daicel Chemical Industries, Ltd., Tokyo, Japan

[21] Appl. No.: 930,094

[22] Filed: Aug. 13, 1992

Related U.S. Application Data

[62] Division of Ser. No. 895,360, Jun. 8, 1992, Pat. No. 5,198,509, which is a division of Ser. No. 728,114, Jul. 10, 1991, Pat. No. 5,169,965.

[30] Foreign Application Priority Data

Jul. 10, 1990 [JP] Japan ................. 2-182124
Aug. 17, 1990 [JP] Japan ................. 2-216569
Nov. 2, 1990 [JP] Japan ................. 2-298482
Nov. 9, 1990 [JP] Japan ................. 2-305829

[51] Int. Cl.$^5$ .............................. C07C 69/74
[52] U.S. Cl. ............................. 560/116; 560/80; 560/84; 560/118; 560/76; 560/127; 560/185; 560/190; 560/193
[58] Field of Search ............... 560/116, 127, 76, 84, 560/185, 190, 193, 116, 118, 80, 84

[56] References Cited

U.S. PATENT DOCUMENTS 3,565,922 2/1971 Rudy et al. ................ 260/348
3,673,156 6/1972 Cevidalli et al. ............ 560/185
4,130,533 12/1978 Lamb ...................... 560/127
4,843,111 6/1989 Yokoshima et al. .......... 560/185
5,032,320 7/1991 Gutierrez et al. ........... 560/76

FOREIGN PATENT DOCUMENTS 0477983 4/1992 European Pat. Off. ........ 560/185
61-78751 4/1986 Japan .................... 260/348
62-33166 2/1987 Japan .................... 260/348
1074217 3/1989 Japan .................... 560/185

OTHER PUBLICATIONS

"Alicyclic epoxy adducts of polylactones...", Fujiwa et al, EP 459,913A2 CA116(16):152600x Dec. 4, 1991. Chem. Abstracts only.

Primary Examiner—Jose' G. Dees
Assistant Examiner—Keith MacMillan
Attorney, Agent, or Firm—Morgan & Finnegan

[57] ABSTRACT

A composition comprising a lactone-modified alicyclic compound (I), or an epoxidized lactone-modified alicyclic compound (II) of the following formulae:

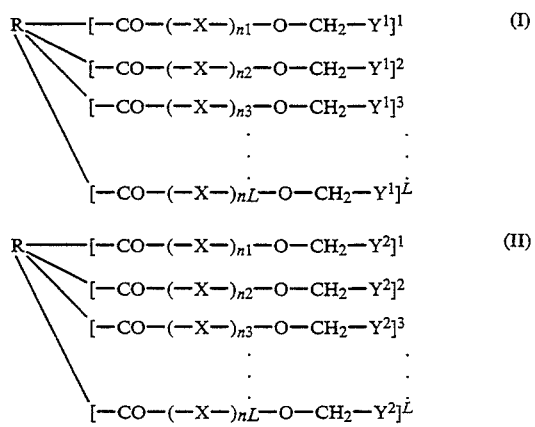

wherein R is an alkyl group, an aromatic group or an alkenyl group having carbon number of from 1 to 30, $Y^1$ is at least one of the structural groups;

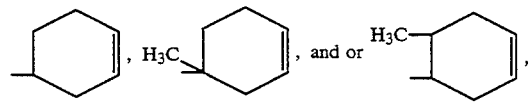

$Y^2$ is at least one of the structural group;

(Abstract continued on next page.)

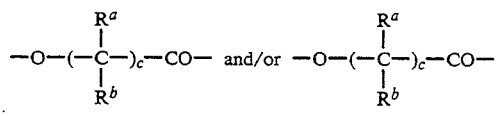

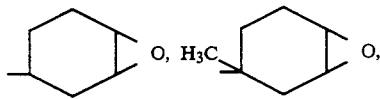

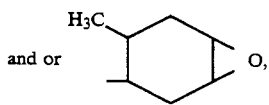

X is the structural group;

and $R^a$ and $R^b$ each independently is hydrogen or a methyl group, c and c′ represent a number of from 4 to 8, from n1 to nL represents 0 or a number of more than 0, respectively, and n1+n2+n3+ . . . +nL corresponds to the total mole numbers of a lactone introduced into one molecule.

These compositions can be made into a heat-curable composition, a photo-curable composition, a polymerizable composition and another photo-curable composition.

5 Claims, 27 Drawing Sheets

LACTONE-MODIFIED ALICYCLIC COMPOSITION AND AN EPOXIDIZED COMPOSITION THEREOF

This is a divisional of co-pending application Ser. No. 07/895,360 filed Jun. 8, 1992, now U.S. Pat. No. 5,198,509, which is a division of Ser. No. 07/728,114 filed on Jul. 10, 1991, now U.S. Pat. No. 5,169,965.

FIELD OF THE INVENTION

The present invention relates to a lactone-modified alicyclic composition, an epoxidized composition thereof and to processes for the preparation thereof, and it further relates to a heat-curable or photo-curable composition, a photo-cationically polymerizable composition etc.

BACKGROUND OF THE INVENTION

The following starting alicyclic compound(V) and the epoxidized compound thereof(VI):

$$Y^1\text{—CO—O—CH}_2\text{—}Y^1 \qquad (V)$$

$$Y^2\text{—CO—O—CH}_2\text{—}Y^2 \qquad (VI)$$

[in the formulae (V) and (VI), $Y^1$ represents at least one structural group selected from

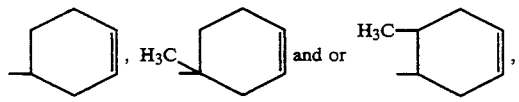

$Y^2$ represents at least one structural group selected from

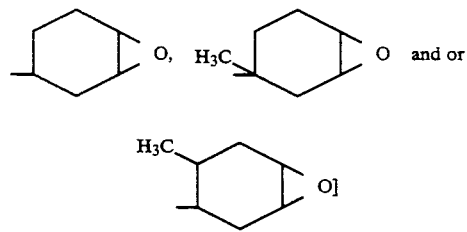

are well-known and have been used as additives for coatings, and as an insulating material or an encapsulating material in the electric fields after being cured with an acid anhydride.

However, the alicyclic epoxy resin (VI) has a poor flexibility for coatings.

Furthermore, the epoxy resin has a disadvantage having a low curing density, resulting in weakness of the coating layers and further causes a problem in finishing-up state at the surface of the coatings.

Still further, there has been a limit in a curing velocity when an acid anhydride is used as a curing agent.

As a result of an intensive investigation, the present inventors have now found that it is possible to solve these problems, by using the present epoxy composition and to improve reactivity and strength in a coating composition or a cured article in which the present epoxy composition is used.

SUMMARY OF THE INVENTION

The present invention is the result of an intensive research in order to develop an excellent component for a coating composition or a cured article, which includes a heat-curable or photo-curable composition, and a photo-cationically polymerizable composition etc.

The primary object of the present invention to solve the problems in the conventional compositions for coating or cured articles, particularly those having poor reactivity and toughness or a poor finished state of the surface of the coating layers.

The present composition has excellent properties enabling it to be used as a resin component, particularly as an epoxy resin component for coating materials, such as a composition for an electro-deposition coating, a powder composition for coating and a baking composition for coatings having high solid contents.

Furthermore, the present composition can be used as a composition capable of being cured at low temperature conditions by addition to a composition composed of a polysiloxane type macromonomer and an organic aluminum or a chelate compound of an organic zirconium compound and after being used for coating, gives an excellent outer appearance and an excellent ductility of the coating layers.

Still further, the present compositions can be used as varnish material for insulating, an LED material or a semiconductor material for encapsulating, etc., in electric material fields.

In addition, the present compositions can be used as a component for a curable composition or a photo-polymerizable composition with a curing agent or a photo-sensitizer, respectively.

DETAILED DESCRIPTION OF THE INVENTION

Figure 1:
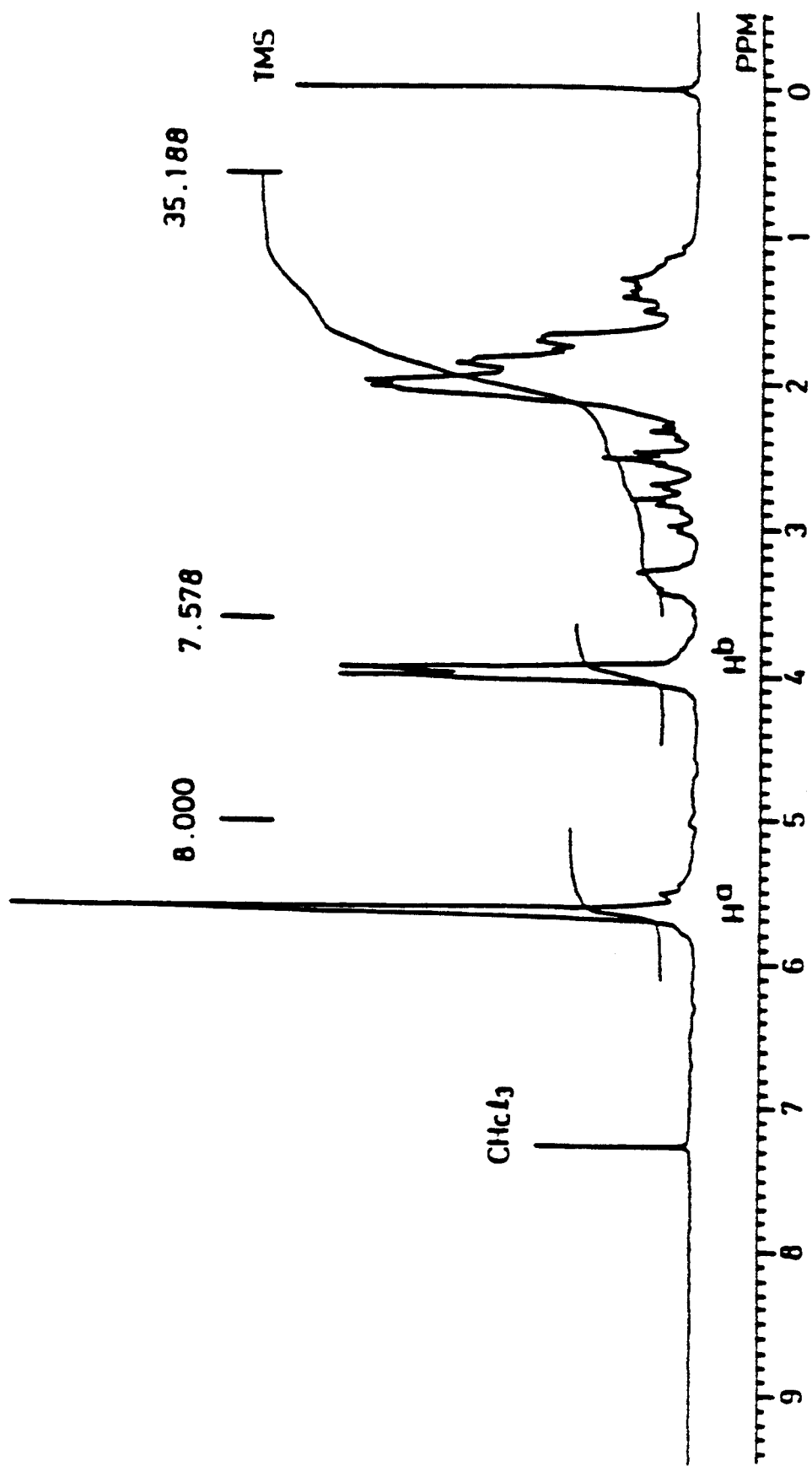
FIG. 1 is a $^1$H-NMR(Nuclear Magnetic Resonance) chart and FIG. 2 is an IR(Infra-Red) spectrum chart, relating to a composition obtained in Synthesis Example 3, respectively.

The present invention will be described hereinafter in more detail.

A first aspect of the present invention relates to a lactone-modified alicyclic compound represented by formula (I) described hereinafter.

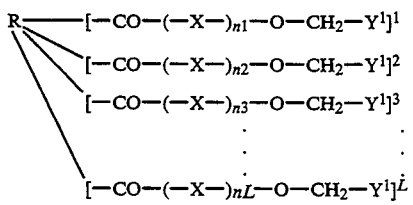
(I)

A second aspect of the present invention, relates to an epoxidized lactone-modified alicyclic compound represented by formula (II) described hereinafter.

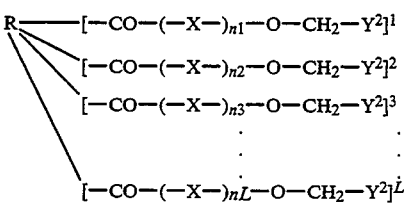
(II)

In the formulae (I) and (II), R represents an alkyl group, an aromatic group or an alkenyl group having carbon number ranging from 1 to 30, which may be an aliphatic or an alicyclic group containing or not a double bond and/or an aromatic group.

More specifically, R is residue group derived from a multi-functional carboxylic acid or an anhydride thereof.

Specific multi-functional carboxylic acid or anhydride thereof include;

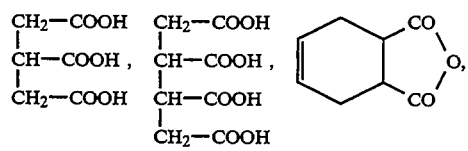

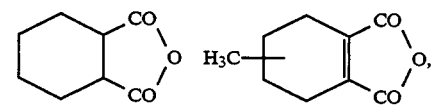

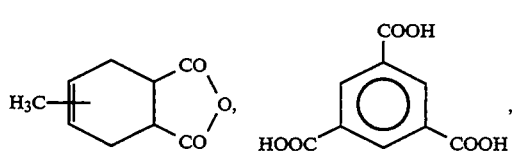

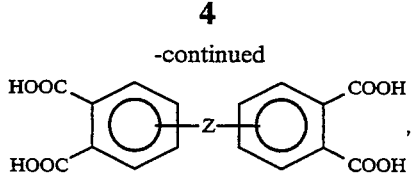

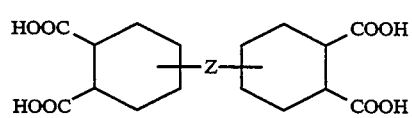

[wherein, Z represents a structural group of —COOCH$_2$CH$_2$OCO—]

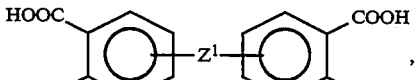

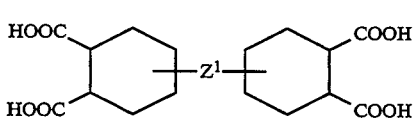

[wherein, $Z^1$ represents a structural group of $$-COOCH_2CHCH_2OCO-,$$
$$\phantom{-COOCH_2CH}OCO-A$$

A represents the following structural group;

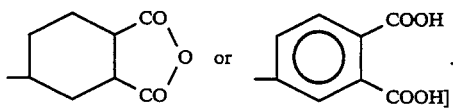

In the formulae (I) and (II), $Y^1$ represents at least one of the following structural groups;

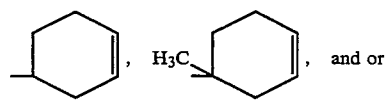

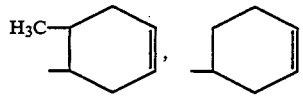

derives from 1,2,5,6-tetrahydrobenzyl-1,2,5,6-tetrahydrobenzoate,

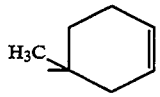

derives from 1-methyl-1,2,5,6-tetrahydrobenzyl-1-methyl-1,2,5,6-tetrahydrobenzoate, and or

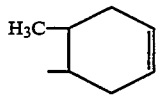

derives from 6-methyl-1,2,5,6-tetrahydrobenzyl-6-methyl-1,2,5,6-tetrahydrobenzoate, respectively.

1,2,5,6-tetrahydrobenzyl-1,2,5,6-tetrahydrobenzoate, 1-methyl-1,2,5,6-tetrahydrobenzyl-1-methyl-1,2,5,6-tetrahydrobenzoate and 6-methyl-1,2,5,6-tetrahydrobenzyl-6-methyl-1,2,5,6-tetrahydrobenzoate, can be prepared by an esterification reaction according to so-called Tischenko reaction of tetrahydrobenzaldehyde, 1-methyl-1,2,5,6-tetrahydrobenzaldehyde and 1-methyl-1,2,5,6-tetrahydrobenzaldehyde, respectively, on a commercial basis.

Tetrahydrobenzaldehyde, 1-methyl-1,2,5 6-tetrahydrobenzaldehyde and 1-methyl-1,2,5,6-tetrahydrobenzaldehyde can be prepared by Diels-Alder reaction of butadiene with acrolein, methacrolein and crotonaldehyde on a commercial basis, respectively.

In the formula (II), $Y^2$ represents at least one of the following structural groups;

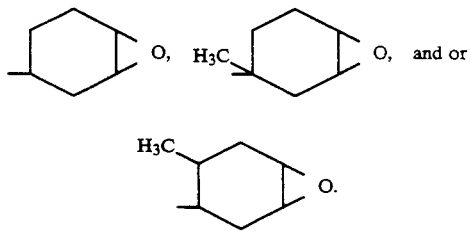

The $Y^2$ derives from $Y^1$ by epoxidation reaction of its double bond with an epoxidation agent such as a peroxide.

In the formulae (I) and (II), X represents the following structural groups;

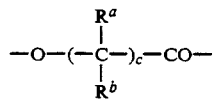

[wherein, $R^a$ and $R^b$ independently each represents hydrogen or a methyl group, respectively, which depends upon the lactone compound used, c represents a natural number of from 4 to 8, which depends upon a lactone compound used].

For example, in the case when epsilon-caprolactone being used as the starting lactone compound, all of $R^a$ and $R^b$ represent hydrogen. Further, in the case when beta-methyl-delta-valerolactone being used as the starting lactone compound, $R^a$ and $R^b$ represent a methyl group or hydrogen, respectively.

In addition, in the case when 3-methyl-caprolactone is used as a starting lactone compound, $R^a$ and $R^b$ represent a methyl group and hydrogen, respectively.

That is, in the case when epsilon-caprolactone being used as a lactone compound, all of the units X in (I) and (II) are —O—(—CH$_2$—)$_5$—CO—, in the case when beta-methylgamma-valero-caprolactone being used as a lactone compound, all of the units X in (I) and (II) are

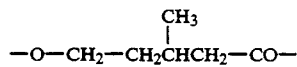

in the case when 3,5,5-trimethylcaprolactone being used as a lactone compound, all of the units X in (I) and (II)

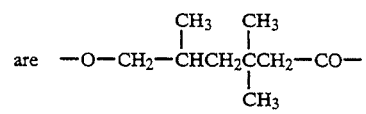

in the case that 3,3,5-trimethylcaprolactone being used as a lactone compound, all of the units X in (I) and (II) are

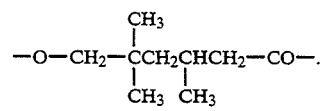

The lactone compound can also be used as a mixture composed of at least two kinds of lactones.

If the mixed lactones are used, the mixed lactone derived units are randomly introduced into the starting compounds.

In the formulae (I) and (II), from n1 to nL represents 0 or a natural number of higher than 0, respectively, and n1+n2+n3+ . . . +nL is 1 or a natural number of higher than 1, which corresponds to the total mol numbers of lactone derived ester-bonding units introduced into one molecule.

If no lactone derived ester-bonding unit is introduced, the mol number n is 0, which corresponds to the starting material, when, 5 mols of the lactone derived ester-bonding unit are introduced, the total mol number n1+n2+n3+ . . . +nL is inevitably 5 in the formulae (I) and (II).

In the formulae (I) and (II), L represents 2 or a natural number of higher than 2, which depends upon the above described multi-functional carboxylic acid or an anhydride thereof, corresponding to a functionality of the carboxylic acid or an anhydride thereof.

For example, if tetrabutanecarboxylic acid is used as the starting multi-functional carboxylic acid, L is inevitably 4.

Further, for example, in the case of tetrahydrophthalic acid or anhydride thereof being used as the starting multi-functional carboxylic acid, L is inevitably 2.

c represents a natural number of from 1 to 7, depending on the starting lactone compound.

For example, in the case of epsilon-caprolactone, beta-methyl-delta-valerolactone or cyclooctanone lactone being used as the starting material, c is 5, 4 or 7, respectively.

It is noted that epsilon-caprolactone can be prepared by a Baeyer-Villiger reaction, in which cyclohexanone is oxidized by a peracid, etc., on a commercial basis.

Furthermore, it is noted that trimethylcaprolactone can be prepared by a Baeyer-Villiger reaction, in which trimethylcyclohexanone is oxidized by a peracid, etc., on a commercial basis.

It is further noted that trimethylcyclohexanone can be prepared by a hydrogenation reaction of isophorone, followed by a Baeyer-Villiger reaction with a peracid to obtain trimethylcaprolactone on a commercial basis.

Beta-methylgamma-valerolactone can be manufactured from 2-hydroxy-4-methyltetrahydropyran as a starting material.

Examples of the peracid include, for example, an organic carboxylic peracid such as performic acid, peracetic acid, perpropionic acid, perbenzoic acid, m-chloroperbenzoic acid, etc., or peracetic acid produced by acetic acid and hydroperoxide and or peracetic acid produced by acetic anhydride and sulfuric acid.

According to other aspects of the present invention, there are provided processes for the preparation of the above compositions which comprise the compounds represented by formulae (I) and (II) described hereinabove.

The above composition which comprises a compound represented by formula (I) can be prepared by an addition reaction of an alicyclic ester compound represented by formula (III) described hereinafter:

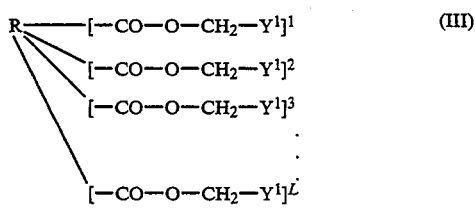

with a lactone compound.

The above ester compound represented by formula (III) can be prepared by an esterification reaction of a multifunctional carboxylic acid represented by general formula;

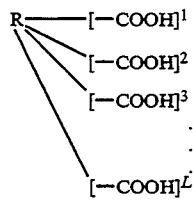

or anhydride thereof, with $Y^1$—$CH_2OH$ [wherein $Y^1$ is at least one structural groups selected from the group of

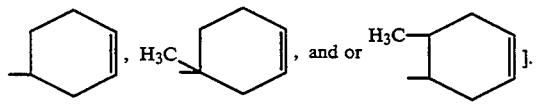

The molar ratio of the $Y^1$—$CH_2OH$ to the multifunctional carboxylic acid or anhydride thereof is preferably more than 1.0, since the reduction velocity of the acid value is higher with excess amount of $Y^1$—$CH_2OH$, provided that unnecessarily excess amount of the $Y^1$—$CH_2OH$ should not be charged because of the need for removal after completion of its reaction.

The starting materials and, in the case of low temperature reaction, several ppm of a titanate catalyst are charged into a reaction vessel equipped with a nozzle for water distillation, etc.

The use of the catalyst is not preferred because of the necessity to remove it.

The esterification reaction can preferably be carried out at a temperature range of 150° to 250° C., from the point of view of a commercially available preparation.

Where the temperature is lower than 150° C., the reaction velocity is too low. On the other hand, at the temperatures higher than 250° C., a considerable thermal decomposition may occur.

In the case of an acid anhydride being used as an acid component of the starting materials, the reaction can be carried out even under relatively low temperatures.

At the start of the reaction, the temperature in the reaction vessel is not raised too much because of the evaporation of water even with excess heating.

The temperature increases as the evaporation of water decreases.

The reaction progress can be monitored by the decrease in the acid value in the reaction vessel.

The above composition which comprises the compound represented by formula (I) can be prepared by an addition reaction of the above described ester compound with a lactone compound.

Reaction conditions for introducing lactone derived ester-bonding units into the ester compound are described in detail hereinafter.

1 mol of the ester compound is allowed to react with a fixed amount of the above described various lactone compounds, specifically from 1 to 20 mols, preferably from 1 to 10 mols.

If the molar ratio is more than 20, the resulting composition which comprises a compound represented by formula (I) cannot provide a resulting epoxy resin having sufficiently good properties, for example, the epoxy resin is too soft.

The reaction for introducing lactone derived ester-bonding units into the ester compound catalysts can be carried out with catalysts such as titanate compounds.

The amount of catalyst to be used is preferably from 0.1 ppm to 10,000 ppm, more preferably from 100 to 2,000 ppm based on the total amount of the starting materials.

If the amount is less than 0.1 ppm, the reaction velocity is too low. On the other hand, even though the amount is more than 10,000 ppm, the reaction velocity is not much improved.

The addition reaction of a lactone compound into the ester compound can also preferably be carried out at a temperature range of from 150° to 250° C. If the temperature is lower than 150° C., the reaction velocity is too low.

On the other hand, if the temperature is higher than 250° C., there may be a thermal decomposition of the lactone compound and coloring.

The above composition which comprises the compound represented by formula (I) can also be prepared by a reaction of the above described multi-functional carboxylic acid or anhydride thereof with a lactone adduct of $Y^1$—$CH_2OH$, that is, $Y^1$—$CH_2O$—(—X—)$_n$—H [wherein X and $Y^1$ are the same structural groups as described hereinabove, n has a distribution of 1 and natural numbers of more than 1].

In carrying out the reaction, $Y^1$—$CH_2OH$ is preferably used together with the starting materials for the purpose of accelerating the acid value reduction. The residual $Y^1$—$CH_2OH$ is preferably removed by distillation after completion of the reaction.

Although other compounds having hydroxyl group can also be used instead of $Y^1$—$CH_2OH$, $Y^1$—$CH_2OH$ is preferred because it has the same structural groups.

The $Y^1$—$CH_2O$—(—X—)$_n$—H can be prepared in a temperature range of 100° C. to 220° C., preferably from 120° C. to 200° C., and in the presence of from 0.1 ppm to 1,000 ppm of a catalyst such as tin compounds, titanate compounds and or tungstic compounds.

The molar ratio of the lactone compound with respect to $Y^1$—$CH_2OH$ can be selected over a wide range.

Furthermore, the above composition which comprises the compound represented by formula (I) can also be prepared by a reaction, in which a multi-functional carboxylic acid or anhydride thereof, $Y^1$—$CH_2OH$ [wherein $Y^1$ is the same structural groups as described hereinabove] and a lactone compound are charged at the same time in the presence of a catalyst into a reaction vessel.

As analysis with IR, GPC and NMR has confirmed that even the compositions obtained by different preparations have the same chemical structures. For example, if butanetetracarboxylic acid is used as a multi-functional carboxylic acid, epsilon-caprolactone is used as a lactone compound and 3-cyclohexene methanol is used as $Y^1$—$CH_2OH$, the lactone-modified alicyclic compound represented by formula (I) corresponds more specifically to the compound of the formula;

$$\begin{array}{l}CH_2-(-CO-[-O-(-CH_2-)_5-CO-]_{n1}-O-CH_2-Y^1)^1 \\ | \\ CH-(-CO-[-O-(-CH_2-)_5-CO-]_{n2}-O-CH_2-Y^1)^2 \\ | \\ CH-(-CO-[-O-(-CH_2-)_5-CO-]_{n3}-O-CH_2-Y^1)^3 \\ | \\ CH_2-(-CO-[-O-(-CH_2-)_5-CO-]_{n4}-O-CH_2-Y^1)^4\end{array}$$

[wherein $Y^1$ is at least one structural groups selected from the group of

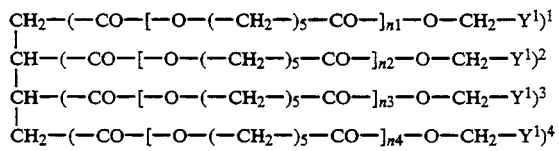

n1, n2, n3 and n4 have a distribution o 0 or a natural number of more than 0, respectively, n1+n2+n3+n4 is 1 or a natural number of more than 1].

Further, the composition which comprises a compound represented by formula (II) is described hereinafter in detail.

The composition which comprises a compound represented by formula (II) can be prepared by epoxidation of the above composition which comprises a compound represented by formula (I).

The epoxidation reaction can be carried out using an epoxidation agent such as a peracid or various hydroperoxides.

The peracids include performic acid, peracetic acid, perpropionic acid, perbenzoic acid and or trifluoroperacetic acid, etc.

Of these peracids, peracetic acid is the preferred epoxidation agent, because it is available on an industrial basis at a moderate price and has a high stability.

The hydroperoxides include hydroperoxide, tertiary butylhydroperoxide, cumenperoxide and metachloroperbenzoic acid, etc.

When carrying out the epoxidation reaction, a catalyst can be used depending on the circumstances.

For example, in the case of peracetic acid being used as an epoxidation agent, an alkali such as sodium carbonate, and an acid such as sulfuric acid, can be used as a catalyst.

On the other hand, when using hydroperoxides, it is possible to obtain a catalytic effect, for example, by using a mixture of tungstic acid and sodium hydroxide together with hydrogen peroxide, or hexacarbonylmolybudenum together with tertiary butyl hydroperoxide.

The epoxidation reaction is carried out in the absence or the presence of a solvent, while controlling the reaction temperature according to the apparatus to be used and the properties of the starting materials.

The temperature range of the epoxidation reaction can be selected according to the reactivity of the epoxidation agent.

In the case of peracetic acid, which is the preferred epoxidation agent, the preferred temperature is from 0° to 70° C.

If the temperature is below 0° C., the reaction velocity is slow, but if the temperature is over 70° C., a decomposition reaction of peracetic acid can occur.

In the case of tertiary butylhydroperoxide/molybdenumdioxide diacetyl acetate, which is an example of a hydroperoxide, the preferable temperature is from 20° C. to 150° C., based on the same consideration.

The use of solvents for dilution is effective for lowering the velocity of ray materials and stabilizing the epoxidation agent.

In the case of peracetic acid being used as the epoxidation agent, a preferred solvent is an aromatic compound, an ether compound and/or an ester compound.

The molar ratio of the epoxidation agent to be used with respect to the unsaturated bonds, is selected in accordance with the proportion of the unsaturated bonds which it is desired to retain.

When preparing epoxy compositions having many epoxy groups, an equal or higher molar ratio of the epoxidation agents with respect to the unsaturated bonds is preferably used, but using amounts of the epoxidation agents at a molar ratio of more than 10 with respect to the unsaturated bonds is not preferable, from a view point of the costs and side reactions described hereinafter.

In the case of peracetic acid, preferred molar ratio is from 1:1 to 5:1. Substituted groups are produced by the side reaction between epoxy groups and acetic acid by-produced and contained in the desired product, depending upon the epoxidation conditions.

The obtained product may also contain other minor by-products, by which a subsequent or a final product can be affected adversely in color hue and acid value.

In order to prevent adverse affects, additives as described hereinafter are preferably used; phosphoric acid, potassium phosphate, sodium phosphate, ammonium hydrogenphosphate, pyrophosphoric acid, potassium pyrophosphate, sodium pyrophosphate, potassium 2-ethylhexyl pyrophosphate, sodium 2-ethylhexyl tripolyphosphate, potassium 2-ethylhexyl tripolyphosphate, tripolyphosphoric acid, potassium tripolyphosphate and or sodium tripolyphosphate, sodium 2-ethylhexyl tetrapolyphosphate, potassium 2-ethylhexyl tetrapolyphosphate.

The use amount of additives used is generally from 10 ppm to 10,000 ppm, preferably from 50 ppm to 1,000 ppm, based on the total weight of the starting materials. It appears that the additives have a chelating effect on metals, which are derived from reaction vessel or materials.

The metals are inactivated by the chelating effect.

The obtained epoxidized product can be separated from a crude reaction mixture by various procedures.

Also, the crude reaction mixture can be obtained by simple removal of solvent, etc., which are low boiling components, even without any purification process.

The removal of the low boiling components is generally carried out at a temperature of from 50° to 200° C., preferably from 80° to 160° C.

Also, the degree of a reduced pressure in the vessel can be adjusted depending upon the boiling points of the solvents used in carrying out the epoxidation reaction.

After completion of the epoxidation reaction, washing the crude solution is preferably washed with water to remove minor amounts of impure components.

During this washing operation, an aromatic compound such as benzene, toluene, xylene, etc., a hydrocarbon such as hexane, heptane, octane, etc., an ester such as ethyl acetate, butyl acetate, etc., can also be used with the water.

The amount of washing water is from 0.1 to 10 multiple amounts, preferably from 1 to 5 multiple amounts, based on the crude reaction solution volume.

Furthermore, an alkali aqueous solution can be used for removing minor amounts of acids, and then water is used again to remove the alkali.

Specifically preferred alkali includes NaOH, KOH, $K_2CO_3$, $Na_2CO_3$, $KHCO_3$, $NaHCO_3$ and $NH_3$. The concentration of the alkali can optionally be selected over a broad range.

The aqueous alkali leaching and subsequent water leaching can be carried out in a temperature range of 10° to 90° C., preferably 10° to 50° C.

After completion of water leaching and succeeding settling, the resultant organic layer is separated from the water layer, followed by distilling out of materials having low boiling points, which are mainly solvents used in the beginning of the reaction, to obtain a product.

Such distillation temperatures are generally between 50° to 200° C., preferably from 80° to 160° C. When distilling out the materials, the degree of reduced pressure can be adjusted as a function of the boiling points of the solvents used.

The reaction can be carried out by either a continuous type or batch type process.

In the case of the batch type process, starting materials and additives such as solvents, etc., are first charged into a reaction vessel, and then an epoxidation agent is added dropwise.

When the reaction crude reaction solution is washed with water after completion of the epoxidation reaction, the solution is separated into two liquid layers.

The organic liquid layer is separated from the water layer in order to evaporate the components having a low boiling point in an evaporator.

In the case of the continuous type process, starting materials, additives such as solvents and an epoxidation agent are supplied continuously into the reaction vessel, and the product is continuously taken out of the vessel.

The preferred type of the reaction vessel includes a piston flow type or a completely mixable type vessel.

For example, in the case of preparing the composition which comprises a compound represented by formula (II), the product obtained is a composition mainly containing the compound represented by the formula (II).

The constitution of the product obtained depends on the constitution of the composition which comprises a compound represented by the formula (I), which is the starting material in the epoxidation reaction.

It appears that the product obtained in the epoxidation reaction with the composition which comprises a compound represented by formula (I) primarily contains the composition which comprises a compound represented by formula (II).

In the case when mixed lactones are used in the addition reaction of lactone derived ester-bonding compound, the mixed lactone units are randomly introduced into the ester compound (III).

Accordingly, the epoxidized composition is also inevitably composed of various compounds having the randomly introduced lactone derived ester-bonding units.

Furthermore, it is noted that an epoxy group is generally ring-opened by water or an acid, even though it is in a minor amount.

Accordingly, the products obtained contain a by-produced compositions, in which $Y^2$ of the (II) is partially converted into $Y^3$.

$Y^3$ specifically represents a ring-opened structural group derived from the epoxy group in $Y^2$, that is,

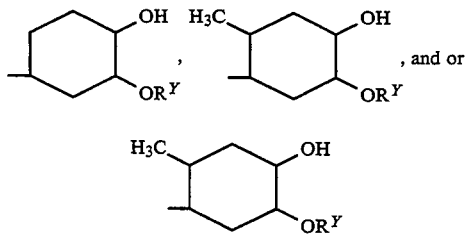

[wherein $R^Y$ represents hydrogen, acetyl group and or propyl group, etc., which depend on the epoxidation agent used].

The product obtained in the epoxidation reaction, in which the compound (II) is a main and desired component, can be used without any treatment.

Furthermore, the composition can optionally be used after purifying, for example, by a chromatography, etc.

According to yet another aspect of the present invention, there are provided a curable composition and a photo-cationically polymerizable vinyl composition consisting essentially of the above composition which comprise compounds represented by formula (II) described hereinabove.

The present curable composition consisting essentially of a composition which comprises a compound represented by formula (II), and a heat-curable agent or a photo-curable agent, will be described hereinafter in detail.

Preferred heat-curable agents specifically include aromatic acid anhydrides such as phthalic anhydride, trimellitic anhydride, pyromellitic anhydride, benzophenonetetracarboxylic anhydride, ethyleneglycol bis-(anhydrotrimellitate), glyceroltris(anhydrotrimellitate), alicyclic acid anhydrides such as maleic anhydride, succinic anhydride, tetrahydrophthalic anhydride, methyltetrahydrophthalic anhydride, methylnadic anhydride, hexahydrophthalic anhydride, methylhexahydrophthalic anhydride, etc., and amines such as ethylenediamine, diethylenetriamine, triethylenetetramine, isophoronediamine, xylenediamine, methaphenylenediamine, diaminodimethyl sulfone, diaminodiphenyl methane, polymethylenediamin, etc., and or imidazoles such as 2-methylimidazole, 2-ethyl-4-methylimidazole, 2-undecylimidazole, 2-heptadecylimidazole, 2-phenylimidazole, etc.

Furthermore, dicyandiamide and derivatives thereof, polyamide resins, organic acid hydrazides, diaminomareonytrile and derivatives thereof, melamine and derivatives thereof, a trifluoroboric compound such as a trifluoroborate-amine complex, a compound having silanolic hydroxyl groups, etc., can be used as a curing agent for epoxy compounds.

Additionally, tertiary amines, esters of boric acid, Lewis acids, organometallic compounds, a salt of an organic acid, etc., can optionally be used together with the above described curing agents as a curing accelerator.

And further, a conventional modifier for epoxy resins and fillers can be added together with the curing agents.

The amount ratio of the curing agent used with respect to the present epoxy composition is generally between 1/0.1 and 1/5, preferably between 1/0.5 and 1/1.5, based on the chemical equivalence, provided that a trifluoroborateamine complex or a compound having silanolic hydroxyl groups is generally used in the chemical equivalence between 1/0.0001 and 1/1.0, preferably between 1/0.001 and 1/1.0.

Furthermore, the alicyclic epoxy composition which comprises a compound represented by formula (II) can be in admixture with other epoxy resins in order to give ductility to the other epoxy resins.

Preferred photo-cationic polymerization initiators specifically include diazonium salts such as

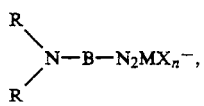 (X)

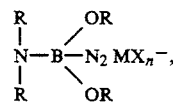 (XI)

sulfonium salts such as $R_3\text{-SMX}_n^-\cdots$ (XII)

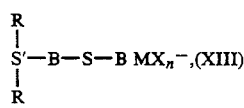 (XIII)

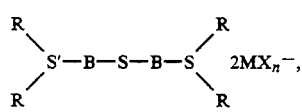 (XIV)

iodonium salts such as $R\text{-}I^+\text{-}RMX_n^-$ (XV) metal complexes such as

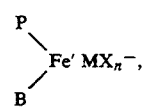 (XVI)

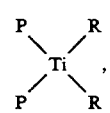 (XVII)

a sulfonium acetone such as

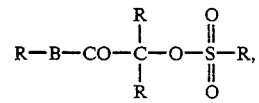 (XVIII)

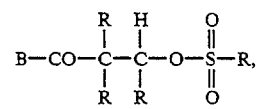 (XIX)

sulfone compounds such as

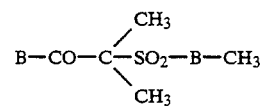 (XX)

[in formulae (X) to (XX), B is

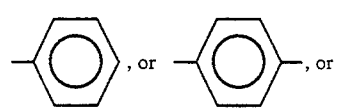

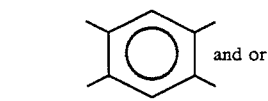

P is

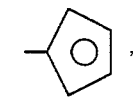

R is hydrogen, an alkyl group, phenyl group, an aryl group and a hydroxyalkyl group, which may be identical or different each other, $MX_n$ is at least one selected from the group consisting of $SbF_6$, $AsF_6$, $PF_6$ and $BF_4$], a silicone compound which is capable of generating a silanol group or a complex of an aluminum compound by photo-irradiation.

The specific silicone compound is preferably a silicone compound having one group selected from the group of peroxysilane, o-nitrobenzyloxy group, alpha-ketosilyl.

The specific silicone compounds having a peroxysilane group are represented by the formula $(R^{x1})_n\text{-Si}(O\text{-}O\text{-}R^{x2})_{4-n}$ [in the formula, $R^{x1}$ and $R^{x2}$ hydrogen, a halogen atom, an alkyl group selected from the group consisting of, for example, methyl, ethyl, n-propyl, isopropyl, n-butyl, t-butyl, sec-butyl, n-pentyl, methoxy group, ethoxy and chloromethyl or an aryl selected from the group of, for example, phenyl, naphthyl, anthranyl, benzyl, which may be identical or different each other, which can have a substituent selected from the group of a halogen atom, nitro, cyano and methoxy, etc., n is a natural number of from 0 to 3].

The silicone compounds have specific formulae described hereinafter;

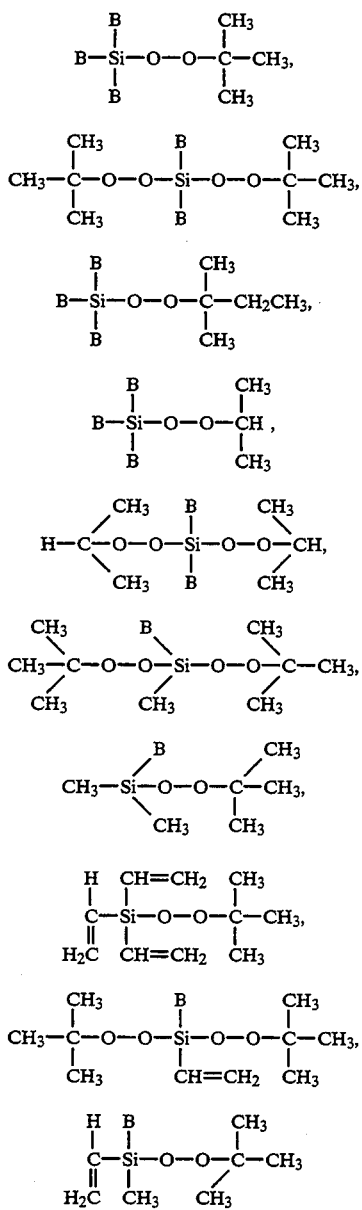

[wherein B represents

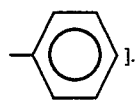].

The specific silicone compound having o-nitrobenzyloxy group is described hereinafter;

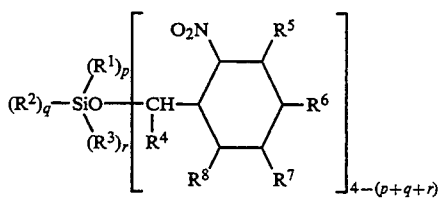

[in the above formula, $R^1$, $R^2$ and $R^3$ are hydrogen, halogen, vinyl, aryl, a substituted or an unsubstituted alkyl having a carbon number of from 1 to 10, an alkoxy having a carbon number of from 1 to 10, a substituted or an unsubstituted aryl, a substituted or an unsubstituted aryloxy and or a siloxy, respectively, which may be identical or different each other, $R^4$ is hydrogen, a substituted or an unsubstituted alkyl having a carbon number of from 1 to 10, a substituted or an unsubstituted phenyl, $R^5$, $R^6$, $R^7$ and $R^8$ are hydrogen, nitro, cyano, hydroxy, mercapto, a halogen, acetyl, an aryl, an alkyl having a carbon number of from 1 to 5, an alkoxy having a carbon number of from 1 to 5, a substituted or an unsubstituted aryl, a substituted or an unsubstituted aryl and or an aryloxy, respectively, which may be identical or different each other, p, q and r are a natural number of from 0 to 3, respectively, and have a relationship of $1 \leq p+q+r \leq 3$]. Substituted or unsubstituted alkyl having a carbon number ranging from 1 to 10 include methyl, ethyl, propyl, n-butyl, t-butyl, pentyl, chloromethyl, chloroethyl, fluoromethyl and cyanomethyl, etc., and alkoxy having a carbon number ranging from 1 to 10 include specifically methoxy, ethoxy, n-propoxy and or n-butoxy, etc.

Substituted or unsubstituted aryl group includes specifically phenyl group, p-methoxyphenyl group, p-chlorophenyl group, p-trifluoromethylphenylvinylmethylphenyl(o-nitrobenzyloxy)silane, t-butylmethylphenyl(o-nitrobenzyloxy)silane, triethyl(o-nitrobenzyloxy)silane, tri(2-chloroethyl)-o-nitrobenzyloxysilane, tri(p-trifluoromethylphenyl)-o-nitrobenzyloxysilane, trimethyl[alpha-(o-nitrophenyl)-o-nitrobenzyloxy]silane, dimethylphenyl[alpha-(o-nitrophenyl)-o-nitrobenzyloxy]silane, methylphenyldi[alpha-(o-nitrophenyl)-o-nitrobenzyloxy]silane, triphenyl(alpha-ethyl-o-nitrobenzyloxy)silane, trimethyl(3-methyl-2-nitrobenzyloxy)silane, dimethylphenyl(3,4,5-trimethoxy-2-nitrobenzyloxy)silane, triphenyl(4,5,6-trimethoxy-2-nitrobenzyloxy)silane, diphenylmethyl(5-methyl-4-methoxy-2-nitrobenzyloxy)silane, triphenyl (4,5-dimethyl-2-nitrobenzyloxy)silane, vinylmethylphenyl(4,5-dichloro-2-nitrobenzyloxy)silane, triphenyl(2,6-dinitrobenzyloxy)silane, diphenylmethyl(2,4-nitrobenzyloxy)silane, triphenyl(3-methoxy-2-nitrobenzyloxy)silane, vinylmethylphenyl(3,4-dimethoxy-2-nitrobenzyloxy)silane, dimethyldi(o-nitrobenzyloxy)silane, methylphenyldi(o-nitrobenzyloxy)silane, vinylphenyldi(o-nitrobenzyloxy)silane, t-butylphenyldi(o-nitrobenzyloxy)silane, diethyldi(o-nitrobenzyloxy)silane, 2-chloroethylphenyldi(o-nitrobenzyloxy)silane, diphenyldi(o-nitrobenzyloxy)silane, diphenyldi(3-methoxy-2-nitrobenzyloxy)silane, diphenyldi(3,4-dimethoxy-2-nitrobenzyloxy)silane, diphenyldi(2,6-dinitrobenzyloxy)silane, diphenyldi(2,4-dinitrobenzyloxy)silane, methyltri(o-nitrobenzyloxy)silane, phenyltri(o-nitrobenzyloxy)silane, p-bis(o-nitrobenzyloxydimethylsilyl)benzene, 1,1,3,3-tetraphenyl-1,3-di(o-nitrobenzyloxy)siloxane, 1,1,3,3,5,5-hexaphenyl-1,5-di(o-nitrobenzyloxy)siloxane.

It is also possible to use a silicone compound produced by a reaction between a SiCL-containing silicone resin and o-nitrobenzyl alcohol, a silicone compound having an alpha-ketosilyl group which is represented by the following formula;

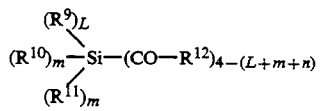

[wherein L, m and n are an integer of 0 to 3, respectively, L+m+n is 3 or less than 3, $R^9$, $R^{10}$ and $R^{11}$ represent a hydrocarbon group such as an alkyl group having a carbon number of from 1 to 10, an aryl group, an allyl group, vinyl group, an allyloxy group and an alkoxy group having a carbon number of from 1 to 10, respectively, which can have a substituent such as a halogen atom, nitro, cyano and or methoxy, which may be identical or different from one another].

Specific compounds having an alpha-ketosilyl group include

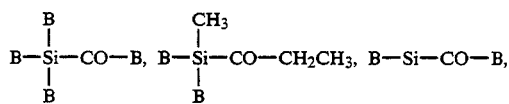

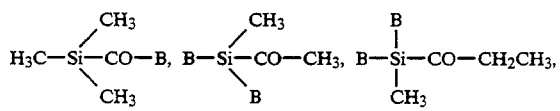

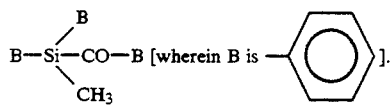

The mixing amount of the above described silicone compound ranges generally from 0.2 to 20% by weight, preferably from 1 to 10% by weight based on the epoxy resin.

Where the amount is smaller than 0.1% by weight, curing of the epoxy resin is not sufficient.

On the other hand, an amount larger than 20% by weight can be used, but it is not preferred because of costs and a problem caused by compounds derived from the decomposition of the catalyst.

Furthermore, an aluminum compound can also be used as a photo-cationic polymerization initiator for the present epoxy compositions.

Specific aluminum compounds include trismethoxy aluminum, trisethoxy aluminum, trisisopropoxy aluminum, trisphenoxy aluminum, trisparamethylphenoxy aluminum, isopropoxy diethoxyaluminum, trisbutoxy aluminum, trisacetoxy aluminum, trisstearato aluminum, trisbutylate aluminum, trispropionato aluminum, trisisopropionato aluminum, trisacetylacetonato aluminum, tristrifluoroacetylacetonato aluminum, trishexafluoroacetylacetonato aluminum, trisethylacetonato aluminum, trissalicylaldehydato aluminum, trisdiethylmalolato aluminum, trispropylacetoacetato aluminum, trisbutylacetoacetato aluminum, trisdipivaloylmethanato aluminum, diacetylacetonatodipivaloylmethanato aluminum.

The above described compounds are represented by following formulae;

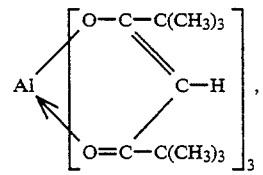

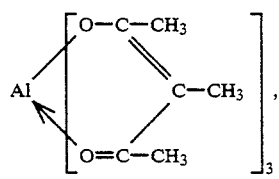

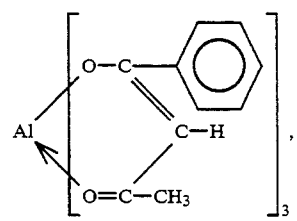

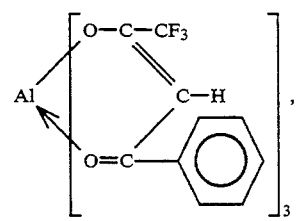

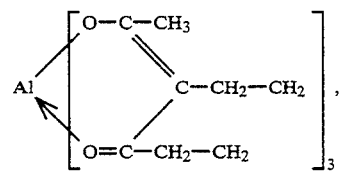

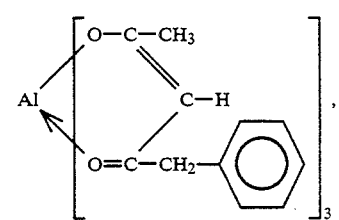

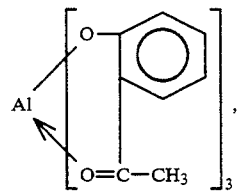

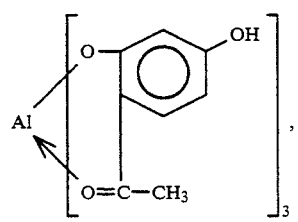

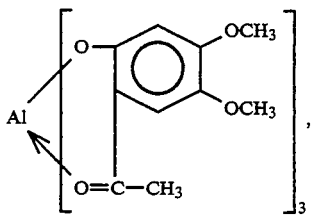

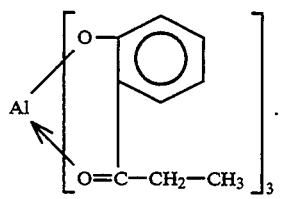

At least one of the above described aluminum compounds can generally be used in an amount ranging from 0.001 to 10% by weight, preferably from 1 to 5% by weight based on the present epoxy composition.

Where the amount is less than 0.001% by weight, sufficient properties, for example, a tensile strength or a tensile elongation, etc., can not be attained in the cured products.

On the other hand, the use amount larger than 10% by weight is not preferred because of costs and a tendency to lower the resistance to moisture.

Various anti-staining agents can be mixed in the present photo-polymerizable composition for increasing a resistance to staining. Anti-staining agents include specifically borates, phosphates, chromates, molybdenum salts, etc.

The anti-staining agents can be used in a proportion of from 10 to 50% by weight, based on the present epoxy composition.

Furthermore, various additives such as coloring dyes or pigments, a silica, an alumina can also be used.

The present photo-polymerizable composition can be coated on a base material and cured by photo-curing at ordinary temperatures or by photo-curing during heating, and postcuring after the photo-curing.

The wavelength of irradiation for photo-curing depends upon a mixing constituents of the present photo-polymerizable composition or the kind of the above described photo-initiator and it is usually from 180 to 700 nm, preferably an ultraviolet wavelength range.

The irradiation period also depends upon mixing constituents of the present photo-polymerizable composition, the kind of the above described photo-initiator and the kind of the irradiation source, specifically it ranges generally from 10 seconds to 30 minutes, preferably, from 20 to 60 seconds.

Furthermore, the temperature for photo-curing during heating also depends upon a mixing constituents of the present photo-polymerizable composition or the kind of the above described photo-initiator, it is usually between 20° to 200° C., preferably, between 60° to 100° C.

Furthermore, the temperature for postcuring after the photo-curing also depends upon a mixing constituent of the present photo-polymerizable composition or the kind of the above described photo-initiator, it ranges usually from 50° to 200° C., preferably, from 100° to 180° C.

A low-voltage mercury lamp, a high-voltage mercury lamp, a carbon arc lamp, a xenon lamp, an argon glow discharge lamp and or a metal halide lamp, etc. can be used, as a discharging source of irradiation.

And also, the present invention provides a photo-cationically polymerizable vinyl composition obtained by the reaction of a composition which comprises a compound represented by the formula (II) described hereinafter:

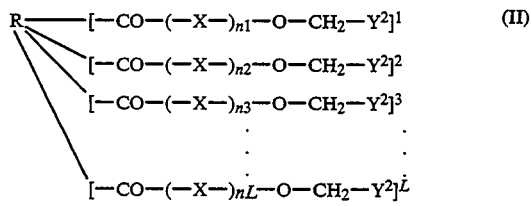

[wherein R, X, n1 to nL, n1+n2+n3+ ... +nL, L and $Y^2$ are all the same structural groups or numbers as described hereinabove] will be described hereinafter in detail.

The present photo-cationically polymerizable vinyl composition can be prepared by a reaction between the composition which comprises a compound represented by formula (II) and an unsaturated carboxylic acid such as acrylic acid or anhydride thereof.

That is, the present photo-cationically polymerizable vinyl composition is a so-called an epoxy acrylate or methacrylate composition.

The present photo-cationically polymerizable vinyl composition has inevitably hydroxyl groups derived from an ring opening reaction of an epoxy group.

The reaction can be carried out by heating in the presence or absence of a ring opening catalyst for an epoxy group such as triethylamine, and optionally a polymerization inhibitor such as hydroquinone monomethylether, a solvent and or a diluent having reactivity.

The reaction is preferably carried out at a temperature range of 50° to 120° C., for example, using acrylic acid as the unsaturated carboxylic acid, approximately 80° to 90° C., under nitrogen gas for the purpose of preventing polymerization.

The reaction ratio of the composition which comprises a compound represented by formula (II) with respect to an unsaturated carboxylic acid ranges preferably from 97/3 to 5/95, more preferably from 95/5 to 30/70 by weight. Where the ratio is more than 97, the flexibility of the cured article is not sufficient.

On the other hand, where the ratio is less than 3, a cured article becomes too soft.

The present photo-cationically polymerizable vinyl composition can also provide the present photo-curable composition as described in detail hereinafter.

The present photo-curable composition can be cured by "radiation" which includes various radiation sources, by which addition polymerizability of vinyl group can be induced.

The present photo-curable composition consists essentially of;

(a) 5 to 95 parts by weight of the photo-cationically polymerizable composition obtained by a composition which comprises a compound represented by formula (II) described hereinafter;

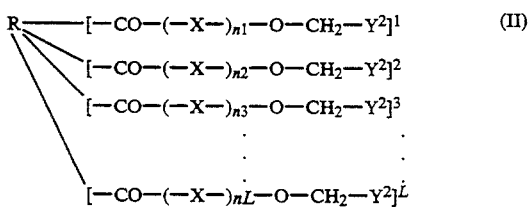

(II)

[wherein R, X, from n1 to nL, n1+n2+n3+ ... +nL, L and $Y^2$ are all the same structural groups or numbers as described hereinabove]

(b) from 95 to 5 parts by weight of a vinyl compound having an ethylenically unsaturated group; and optionally (c) a photosensitizer.

The compound having an ethylenically unsaturated group specifically includes styrene, an acrylic or methacrylic ester compound, N-vinylpyrolidone, etc., which have a radically polymerizable double bond and which are liquid compounds having low viscosity.

The compound is represented by general formula described hereinafter; $(CH_2=CX-CO-O)_n-R$ [wherein X is hydrogen or methyl group, R is an alcohol having the number functionality of n, n is a natural number ranging from 1 to 8].

The acrylic or methacrylic ester compound includes 2-hydroxyethyl acrylate, 2-hydroxyethyl methacrylate, 3-hydroxypropyl acrylate, 3-hydroxypropylmethacrylate, an acrylic ester of tetrahydrofulfuryl alcohol, a methacrylic ester having mono-functionality such as phenoxyethyl acrylate, an acrylic or methacrylic ester having two-functionality such as diacrylate of 1,6-hexanediol, dimethacrylate of 1,6-hexanediol, diacrylate of propyleneglycol, dimethacrylate of propyleneglycol, diacrylate of neopentylglycol, etc., an acrylic or mothacrylic ester having three-functionality such as triacrylate of trimethylolpropane, triacrylate of pentaerythrytol, etc.

The above compound having an ethylenically unsaturated group can be also used as a mixture.

Preferred photosensitizer includes benzophenone, acetophenonebenzyl, benzylmethylketone, benzoin, benzoin methylether, benzoin ethylether, benzoin isopropylether, benzoin isobutylether, dimethoxyacetophenone, diethoxyacetophenone, dimethoxyphenylacetophenone, diphenyldisulfide and or alphaalkyl benzoin, etc., which are well-known in the photocuring field.

The amount of the photosensitizer used is preferably approximately 0.01 to 10%, more preferably approximately from 0.1 to 5% by weight based on the total weight of the present curable composition.

The curing process can also be carried out by a conventional method in the photo-curing field.

An acceleration agent for inducing a radical which has a polymerizability through absorption of a photoenergy can be used together with the photosensitizer, which is, for example, tertiary amines.

The present photo-curable composition can also include various additives such as a heat polymerization inhibitor, a surfactant, an ultraviolet ray absorbent, a delustering agent, a thixotropic agent and a dye or pigment, etc., and further various thermoplastic resins or thermosetting resins.

The present photo-curable composition is coated on a substrate material as thin layer, that it is cured.

The coating on the substrate can be carried out by spraying, brushing, dipping and or roll coating.

Curing by radiation can preferably be carried out in the presence of an inert gas such as nitrogen gas, and also even in air.

The present photo-curable composition can be cured by "photo-radiation" such as a chemical ray having a rave length of preferably 200 to 7,500 A, more preferably 2,000 to 4,000 A.

The chemical rays can be produced from various photo-radiation sources such as sun light, carbon arc light and/or mercury vapor light which are artificial photo-sources.

The following Examples are given to illustrate the practice of this invention but they are not intended in any ray to act to limit the scope of this invention.

SYNTHESIS EXAMPLE 1

A reaction vessel equipped with a stirrer, a condenser for cooling and a tube for supplying nitrogen gas was charged with 991.0 g. of 3-cyclohexene 1-methanol and 1,006.0 g. of epsilon-caprolactone.

2.0 g. of epsilon-caprolactone solution containing 1% of stannous chloride was added to the reaction vessel.

The contents in the vessel were gradually raised to a temperature of 170° C. over 2 hours under the presence of nitrogen gas.

The temperature was maintained for 7 hours to alloy reaction of the contents, and then cooled to room temperatures.

An epsilon-caprolactone adduct was obtained.

It was confirmed by gas chromatography analysis that 0.15% of unreacted epsilon-caprolactone is left in the adduct.

SYNTHESIS EXAMPLE 2

The same procedure as described in Synthesis Example 1 was repeated, except that 660.7 g. of 3-cyclohexene 1-methanol and 1,341.3 g. of epsilon-caprolactone were used to obtain an epsilon-caprolactone adduct. It was confirmed by gas chromatography analysis that 0.10% of unreacted epsilon-caprolactone remained in the adduct.

SYNTHESIS EXAMPLE 3

A reaction vessel equipped with a stirrer and a tube for distilling water was charged with 468.3 g. of 1,2,3,4-butanetetracarboxylic acid and 1,473.9 g. of 3-cyclohexene 1-methanol.

The contents in the reaction vessel were gradually raised to a temperature of 150° C. over 1 hour, and as a result, the contents became roughly homogeneous, then water distillation was started.

Additionally, the reaction temperature was raised to 220° C. over approximately 3 hours, and further reaction was continued for approximately 20 hours.

Successively, the contents were cooled to a temperature of 140° C., and then excess 3-cyclohexene 1-methanol was distilled out of the reaction system under a pressure reduction degree range of from 1 to 10 mm Hg, to obtain 1,220 g. of a product.

The product obtained was liquid at room temperature, in which less than 0.1% of 3-cyclohexene 1-methanol remained as determined by gas chromatography analysis.

It was confirmed that the esterification reaction was almost completed, because an acid value of the product was reduced to 0.90.

Figure 2:
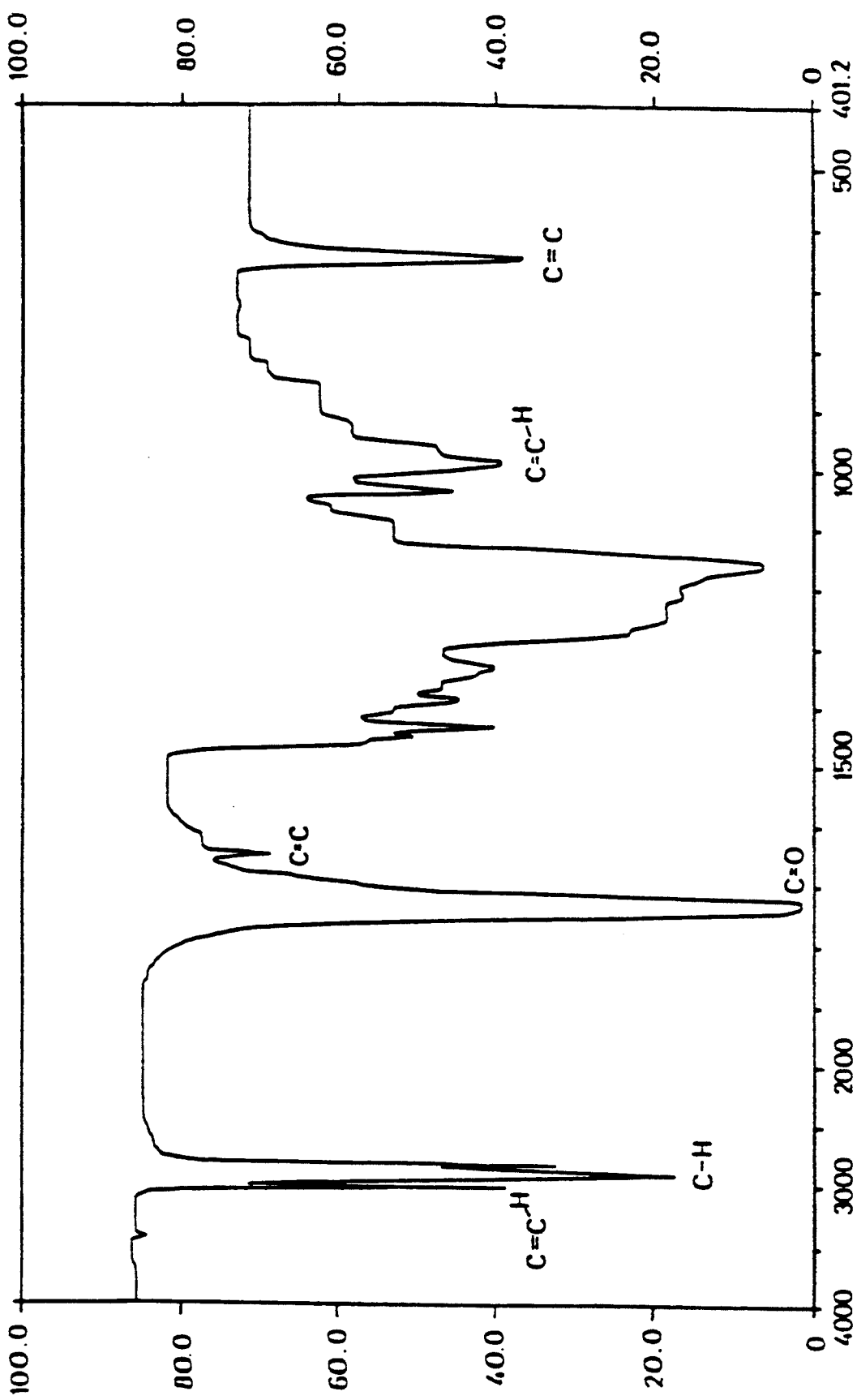

Successively, the product obtained was analyzed with a $^1$H-NMR equipment and an IR spectrometer. The spectra are shown in FIG. 1 and FIG. 2, respectively.

The H-NMR spectrum chart was obtained with CDCl$_3$ as a solvent, at room temperature using JNM-EX 90 equipment (manufactured by Nihon Denshi, Ltd.).

In the NMR spectrum chart, a singlet delta 5.67 is derived from a hydrogen bonded to a carbon atom having double bonds, and a multiplet delta 3.99(J=5.5 HZ) is derived from a hydrogen of the methylene group which is adjacent to an oxygen atom.

No signal due to acid proton was observed.

The IR spectrum chart was obtained using IR-435 spectrometer (manufactured by Shimadzu Seisakusyo, Ltd.), and NaCl plate on which the above product sample was coated.

An absorption peak was observed at 1,733 cm$^{-1}$, which is derived from carbonyl group, absorption peaks were observed at 3,110 cm$^{-1}$, 1,647 cm$^{-1}$ 991 cm$^{-1}$ and 652 cm$^{-1}$, which are derived from double bonds.

It is noted that an absorption peak which is derived from hydroxyl group in the vicinity of 3,500 cm$^{-1}$ had disappeared.

The above analyses confirmed that the product is represented by the general formula described hereinafter by the above analyses;

$$\begin{array}{l} CH_2-COO-CH_2-Y^1 \\ | \\ CH-COO-CH_2-Y^1 \\ | \\ CH-COO-CH_2-Y^1 \\ | \\ CH_2-COO-CH_2-Y^1 \end{array}$$

[wherein Y$^1$ represents

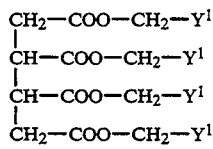

].

EXAMPLE 1

A reaction vessel equipped with a stirrer and a tube for distilling water was charged with 1,475 g, of 1,2,3,4-butanetetracarboxylic acid, 3,106 g. of 3-cyclohexene 1-methanol and 1072.0 g. of the lactone adduct obtained in Synthesis Example 2.

The contents in the reaction vessel yore gradually raised to a temperature of 150° C. over 3 hours and as a result, the contents were roughly homogeneous, then water distillation was started.

Additionally, the reaction temperature was raised to 220° C. over approximately 2 hours, and further reaction was continued for approximately 37 hours.

Successively, the contents were cooled to a temperature of 140° C., and then excess 3-cyclohexene 1-methanol was distilled out of the reaction system over approximately 3 hours under a reduced pressure ranging from 1 to 10 mm Hg, to obtain 4,560 g. of a product.

The product obtained was liquid at room temperatures, in which less than 0.1% of 3-cyclohexene 1-methanol remained as determined by gas chromatography analysis.

It was confirmed that the esterification reaction was almost completed, because an acid value of the product was reduced to 1.0.

Successively, the product obtained was analyzed with a $^1$H-NMR, an IR spectrometer and a GPC equipment(gel permeation chromatography).

Figure 3:
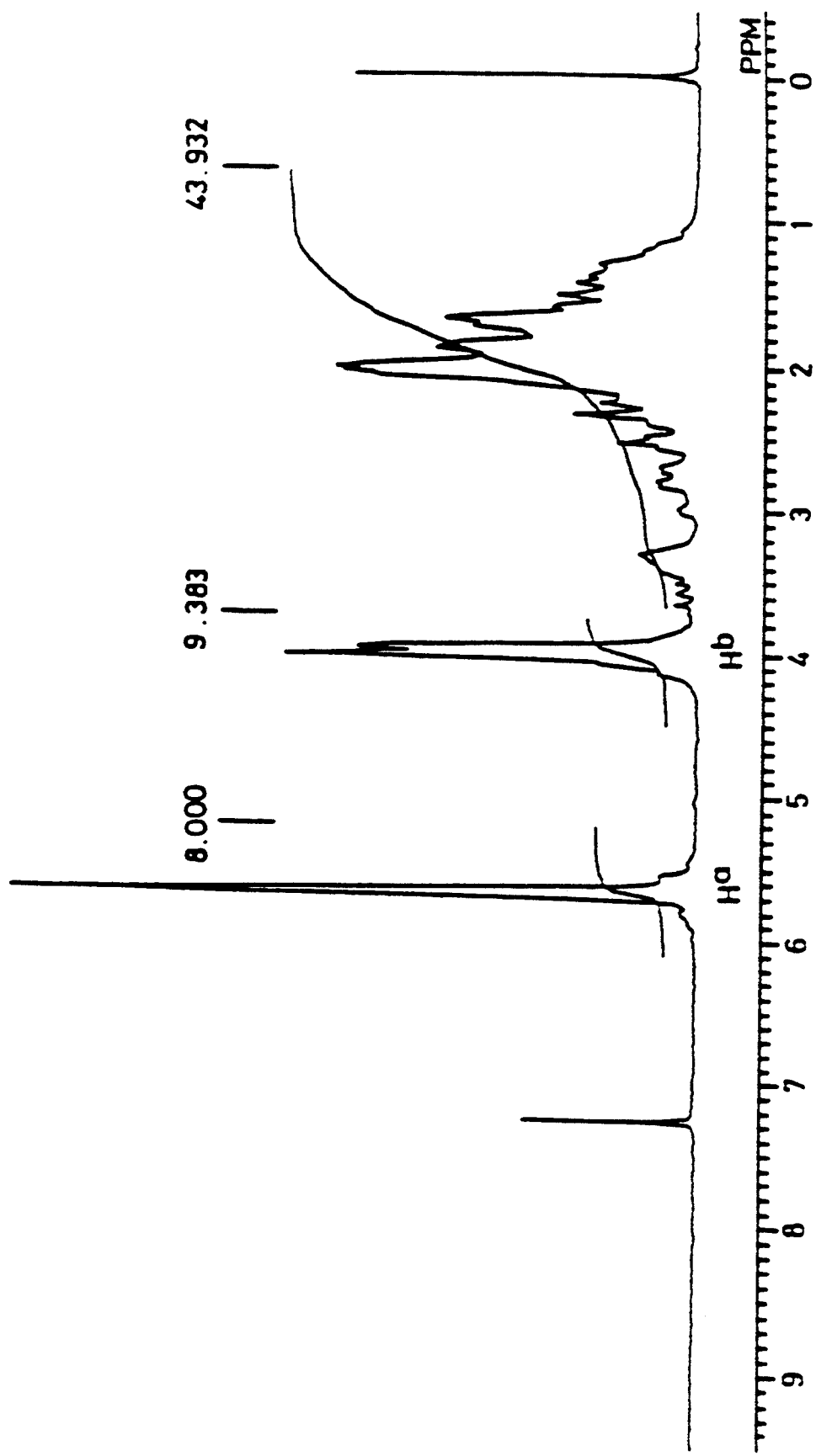
FIG. 3 is $^1$H-NMR chart.
Figure 4:
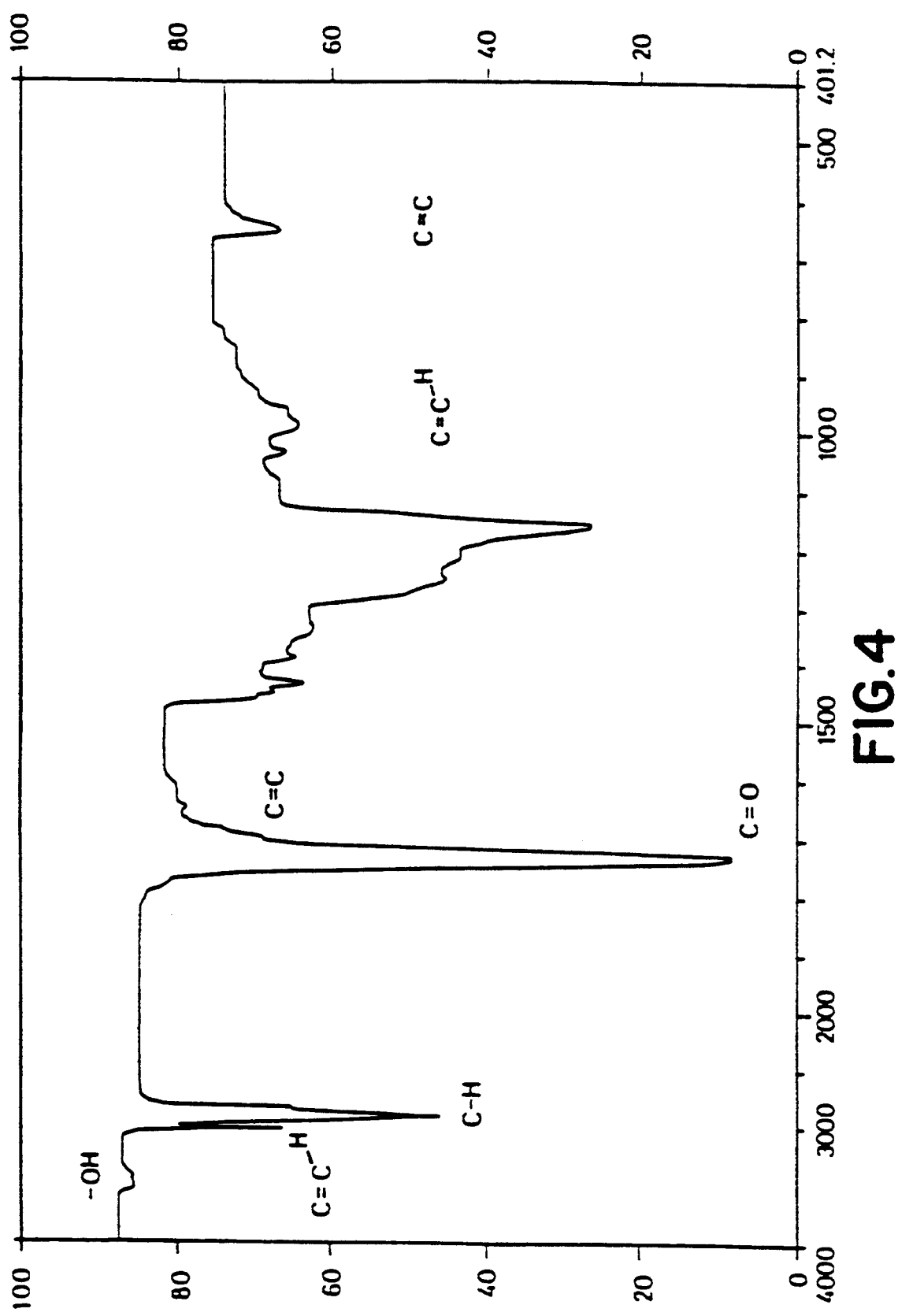
FIG. 4 is an IR spectrum chart and FIG. 5 is a GPC(Gel Permeation Chromatography) chart relating to a composition obtained in Example 1, respectively.
Figure 5:
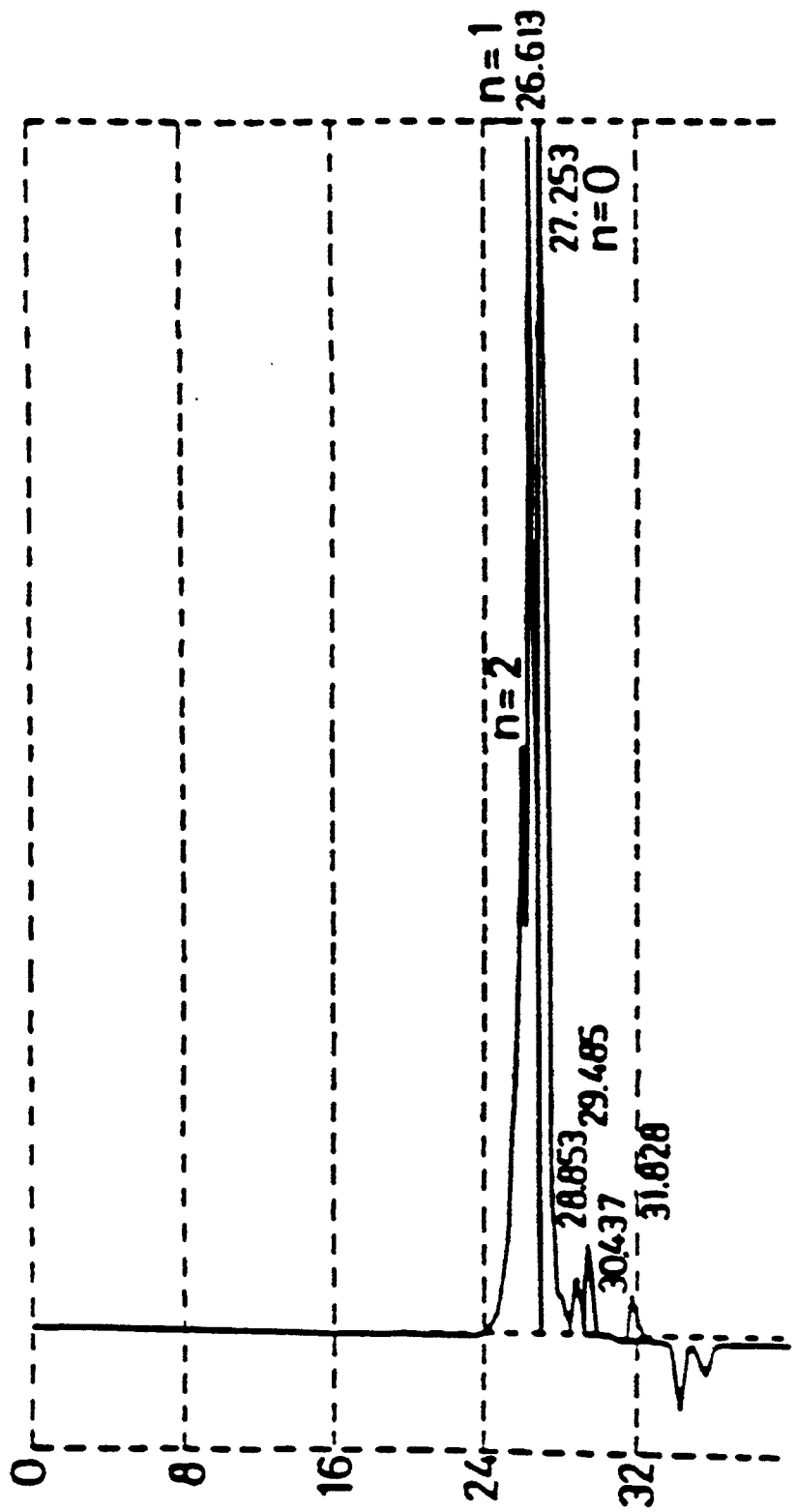

The spectrum charts are shorn in FIG. 3, FIG. 4 and FIG. 5, respectively.

In the NMR spectrum chart(FIG. 3), a singlet delta 5.67 is derived from a hydrogen bonded to a carbon atom having double bonds, and a multiplet delta 3.8 to 4.2 is derived from a hydrogen of the methylene group which is adjacent to oxygen atom.

No signal due to acid proton was observed.

In the IR chart(FIG. 4), an absorption peak was observed at 1,731 cm$^{-1}$, which is derived from carbonyl group, and absorption peaks were observed at 3,017 cm$^{-1}$, 1,660 cm$^{-1}$ 988 cm $^{-1}$ and 651 cm$^{-1}$, which are derived from double bonds.

An absorption peak 3,500 cm$^{-1}$, which peak is derived from hydroxyl group was found to have disappeared.

The GPC chart(FIG. 5) illustrates that the product is a mixture composed of a compound into which no epsilon-caprolactone derived ester-bonding unit is introduced(n=0), a compound into which one mol of epsilon-caprolactone derived ester-bonding unit is introduced(n=1), a compound into which 2 mol of epsilon-caprolactone derived ester-bonding unit is introduced(n=2), and compounds which have a distribution(n=3,4,5 . . . ) of more than 2 mol of epsilon-caprolactone derived ester-bonding unit.

The above analyses confirmed that the product is represented by the general formula described hereinafter;

$$\begin{array}{l} CH_2-CO[-O-(CH_2)_5-CO-]_{n1}-O-CH_2-Y^1 \\ | \\ CH-CO[-O-(CH_2)_5-CO-]_{n2}-O-CH_2-Y^1 \\ | \\ CH-CO[-O-(CH_2)_5-CO-]_{n3}-O-CH_2-Y^1 \\ | \\ CH_2-CO[-O-(CH_2)_5-CO-]_{n4}-O-CH_2-Y^1 \end{array}$$

[wherein Y$^1$ represents

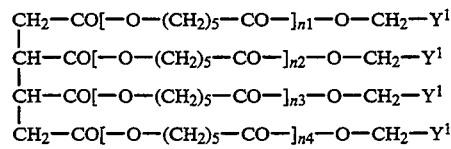

, n1 + n2 + n3 + n4 = 1].

EXAMPLE 2

A reaction vessel equipped with a stirrer and a tube for distilling water was charged with 468.3 g. of 1,2,3,4-butanetetracarboxylic acid and 224.3 g. of 3-cyclohexene 1-methanol and 1,357.2 g. of the adduct obtained in Synthesis Example 1.

The contents in the reaction vessel yore gradually raised to a temperature of 150° C. over 1 hour and, as a result, the contents became roughly homogeneous, followed by initiation of water distillation.

Additionally, the reaction temperature was raised to 220° C. over approximately 3 hours, and further reaction was continued for approximately 38 hours while removing water.

Successively, the contents were cooled to a temperature of 140° C., and then excessively charged 3- cyclohexene 1-methanol was distilled out of the reaction system over approximately 3 hours under a reduced pressure ranging of from 1 to 10 mm Hg, to obtain 1,904 g. of a product.

30.1% of unreacted 3-cyclohexene 1-methanol remained in the product obtained as determined by gas chromatography analysis.

It was confirmed that the esterification reaction was almost completed, because an acid value of the product was reduced to 0.5.

Successively, the product obtained was analyzed with a $^1$H-NMR, an IR spectrometer and a GPC equipment.

Figure 6:
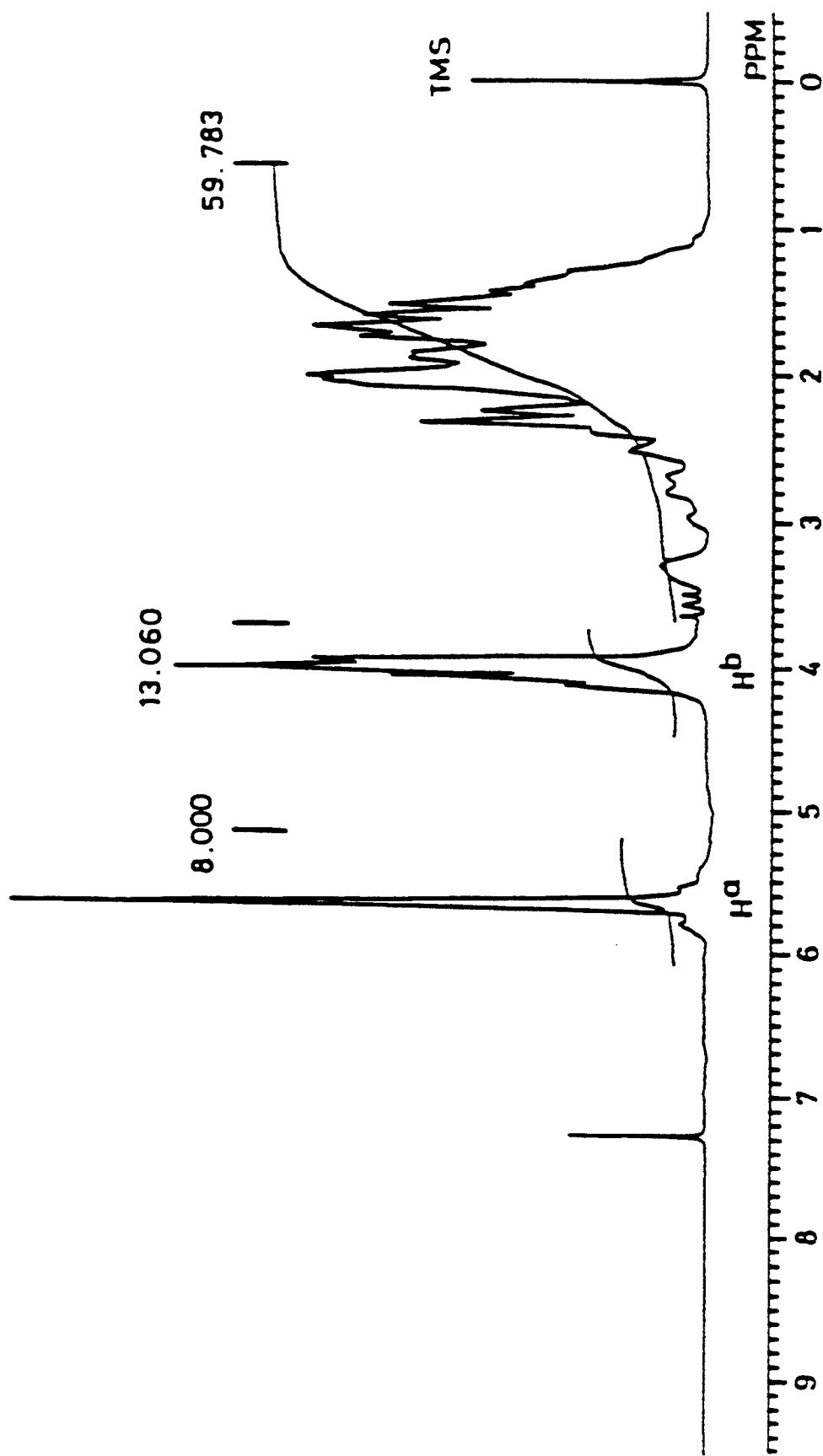
FIG. 6 is $^1$H-NMR chart.
Figure 7:
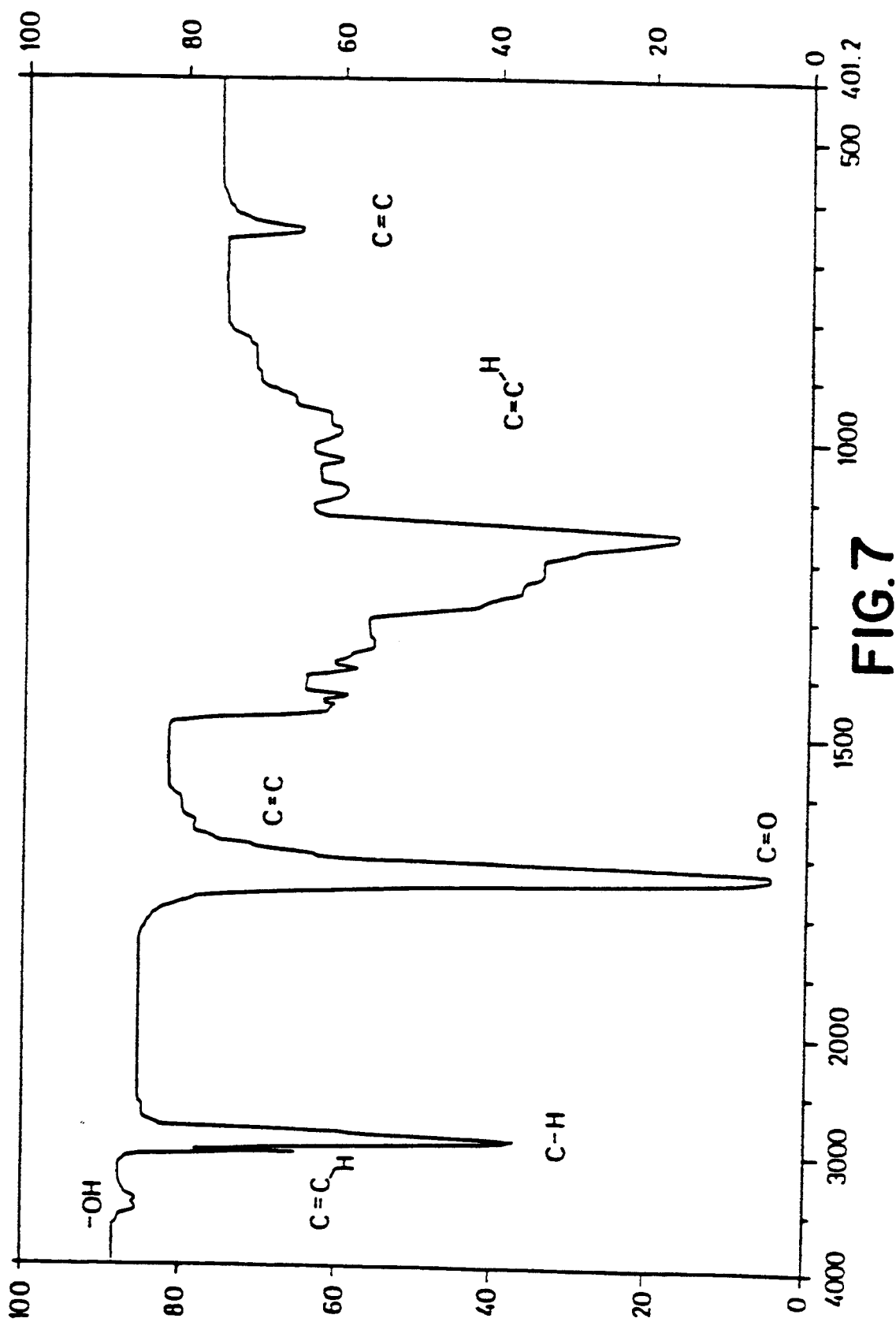
FIG. 7 is an IR spectrum chart and FIG. 8 is a GPC chart relating to a composition obtained in Example 2, respectively.
Figure 8:
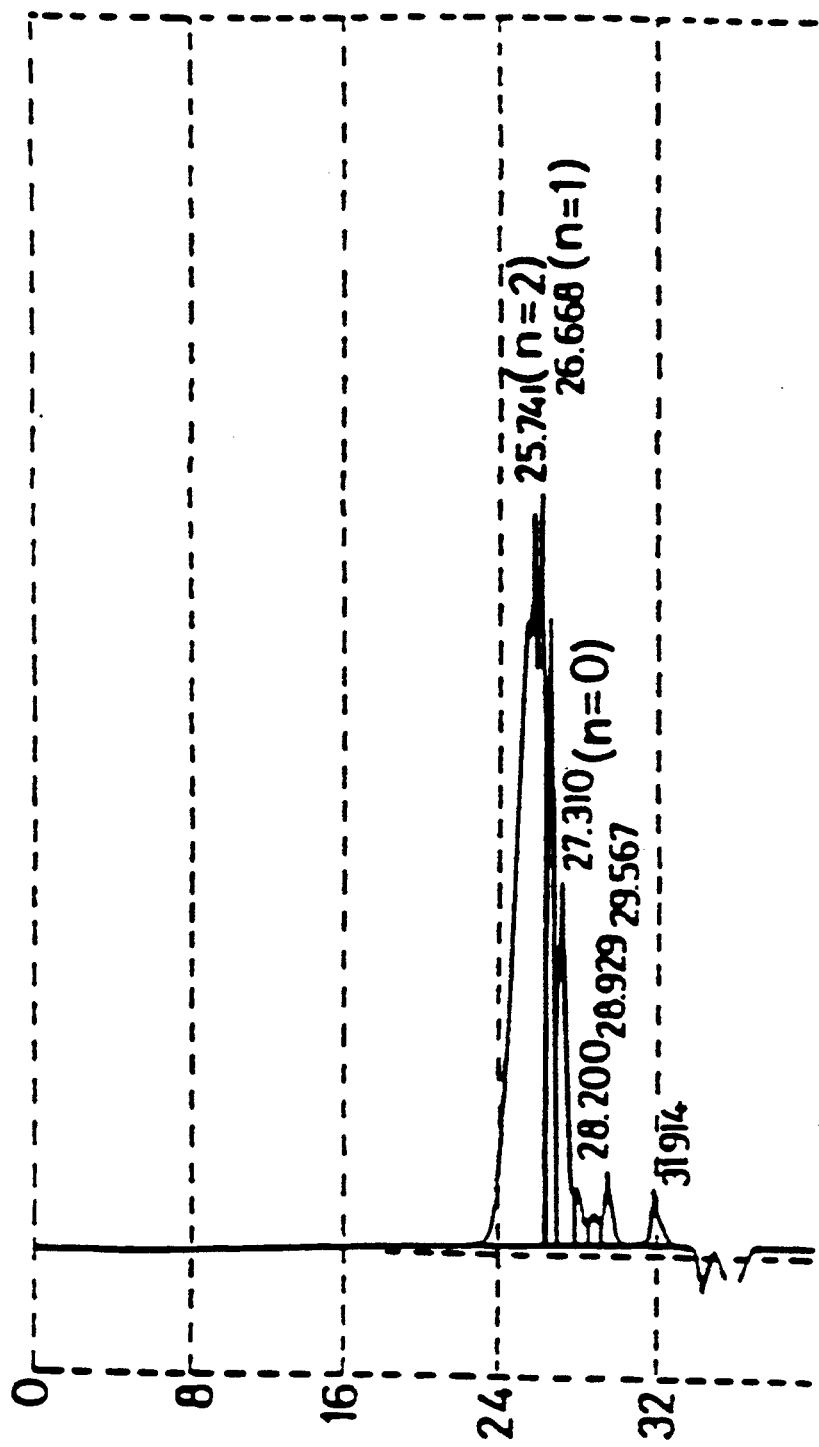

The spectrum charts are shown in FIG. 6, FIG. 7 and FIG. 8, respectively.

In the NMR spectrum chart(FIG. 6), a singlet delta 5.67 is derived from a hydrogen bonded to a carbon atom having double bonds, and a multiplet delta 3.8 to 4.2 is derived from a hydrogen of the methylene group which is adjacent to oxygen atom.

No signal due to acid proton was observed.

In the IR chart(FIG. 7), an absorption peak was observed at 1,734 cm$^{-1}$, which is derived from carbonyl group and absorption peaks were observed at 3,018 cm$^{-1}$, 1,659 cm$^{-1}$, 988 cm$^{-1}$ and 669 cm$^{-1}$, which are derived from double bonds.

An absorption peak around 3,500 cm$^{-1}$ is derived from hydroxyl group was found to have disappeared.

The GPC chart (FIG. 6) illustrates that the product is a mixture composed of a compound into which no epsilon-caprolactone derived ester-bonding unit is introduced(n=0), a compound into which one mol of epsilon-caprolactone derived ester-bonding unit is introduced(n=1), and compounds which have a distribution(n=2,3,4, . . . ) of more than 1 mol of epsilon-caprolactone derived ester-bonding unit.

The above analyses confirmed that the product is represented by the general formula described hereinafter;

$$\begin{array}{l} CH_2-CO[-O-(CH_2)_5-CO-]_{n1}-O-CH_2-Y^1 \\ | \\ CH-CO[-O-(CH_2)_5-CO-]_{n2}-O-CH_2-Y^1 \\ | \\ CH-CO[-O-(CH_2)_5-CO-]_{n3}-O-CH_2-Y^1 \\ | \\ CH_2-CO[-O-(CH_2)_5-CO-]_{n4}-O-CH_2-Y^1 \end{array}$$

[wherein $Y^1$ represents

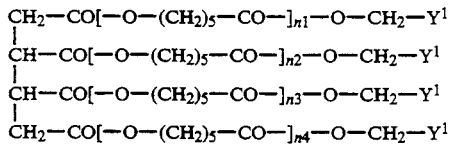

, n1 + n2 + n3 + n4 = 3].

EXAMPLE 3

A reaction vessel equipped with a stirrer and a reflux condenser was charged with 610.0 g. of the product obtained in Synthesis Example 3,114.7 g. of epsilon-caprolactone and 0.36 g. of a heptane solution containing 1% of tetrabutyltitanate.

The contents in the reaction vessel were gradually raised to a temperature of 220° C. over 1 hour.

Further reaction was continued over approximately 35 hours, followed by being cooled to obtain a composition having the same distribution pattern as in Example 1, as a result of GPC analysis.

Figure 9:
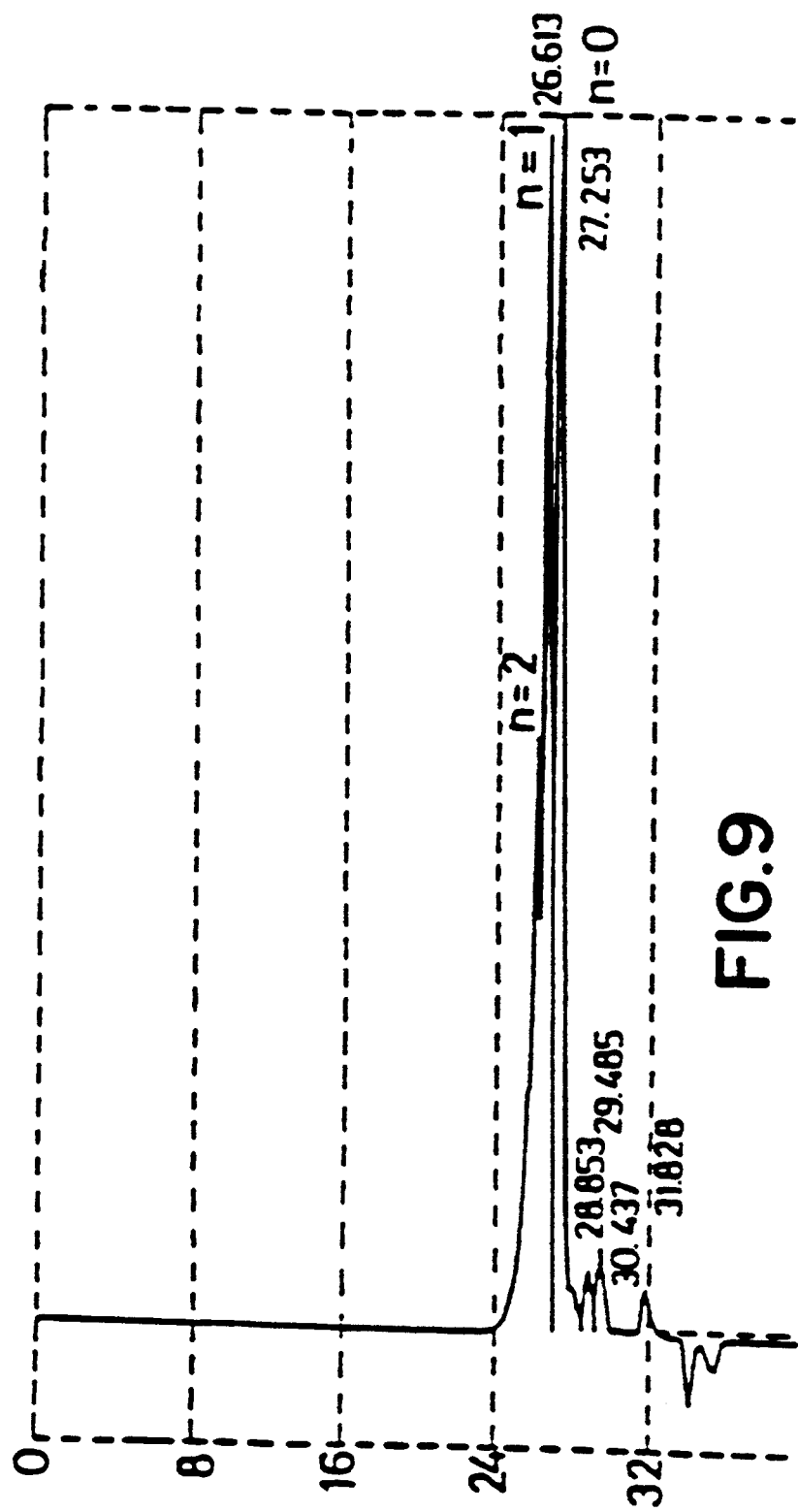
FIG. 9 is a GPC chart relating to a composition obtained in Example 3.

The GPC spectrum is illustrated in FIG. 9.

EXAMPLE 4

A jacketed-reaction vessel equipped with a reflux condenser, a funnel for dropwise addition, an inlet for supplying peracetic acid and a tube for supplying nitrogen gas was charged with 1,760.5 g. of the product obtained in Example 2 and 1,000 g. of ethyl acetate.

Subsequently, a funnel for dropwise addition was charged with 2,952.8 g. of ethyl acetate solution containing 30% of acetic acid, and 3.0 g. of 2-ethylhexyl sodium tripolyphosphate was dissolved as a stabilizer.

The peracetic acid and ethyl acetate solution of the stabilizer was added into the ethyl acetate containing peracetic acid and the product in Example 2 while maintaining a reaction temperature of 40° C. over approximately 4 hours.

Further reaction temperature of 40° C. was maintained over approximately 3 hours.

Successively, 7,000 g. of pure water was added to the solution.

After stirring for 30 minutes, the solution was allowed to stand without stirring at the temperature of 40° C. to separate into two liquid layers. After 30 minutes, the lower liquid layer was gradually removed from upper liquid.

Successively, 2,000 g. of ethyl acetate was added into the upper liquid, and then 7,000 g. of pure water was added, followed by being stirred for 30 minutes and settled to remove a resulting lower layer.

In addition, 7,000 g. of pure water was added into the upper liquid layer and stirred at a temperature of 40° C. for 30 minutes and allowed to settle in order to remove a resulting lower layer.

The upper liquid layer obtained was supplied into a thin-film evaporator maintained at a temperature of 120° C. and a pressure reduction degree of 50 mm Hg, with supplying speed of 300 cc/hour to obtain 1,800 g. of a product.

The product exhibited the properties described hereinafter.

| | |
|---|---|
| Color hue (APHA) | 40 |
| Oxirane oxygen concentration (%) | 8.2 |
| Acid value (mg KOH/g) | 0.8 |
| Viscosity (cp/70° C.) | 2,200 |

Subsequently, the product obtained was analyzed with a $^1$H-NMR, an IR spectrometer and a GPC equipment.

Figure 10:
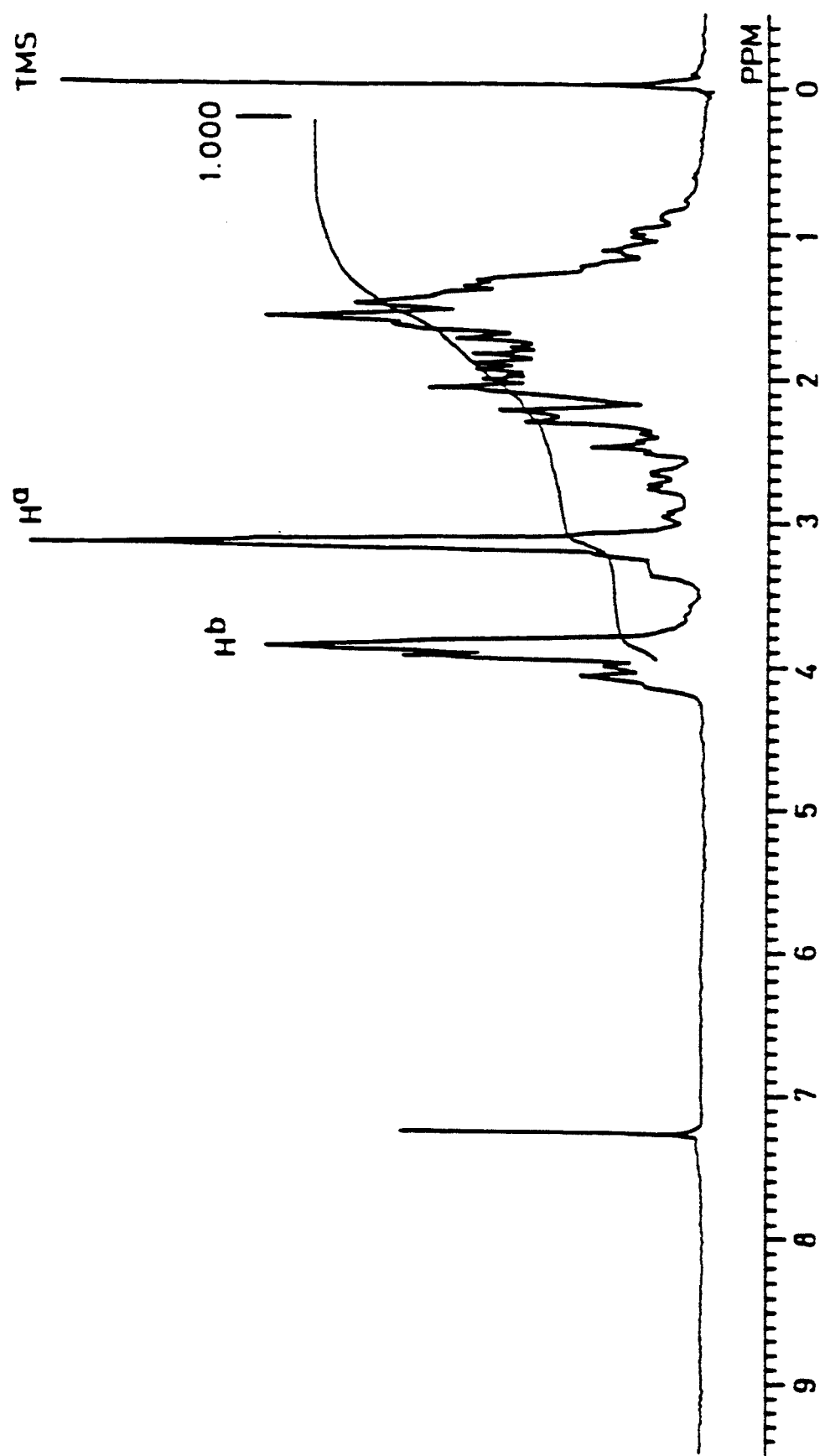
FIG. 10 is $^1$H-NMR chart.

In the NMR spectrum chart(FIG. 10), a multiplet delta 3.1 is to 3.3(H$^a$) is derived from a methylene hydrogen in epoxy ring, and a multiplet delta 3.8 to 4.1(H$^b$) is derived from a hydrogen of methylene group which is adjacent to oxygen atom.

Figure 11:
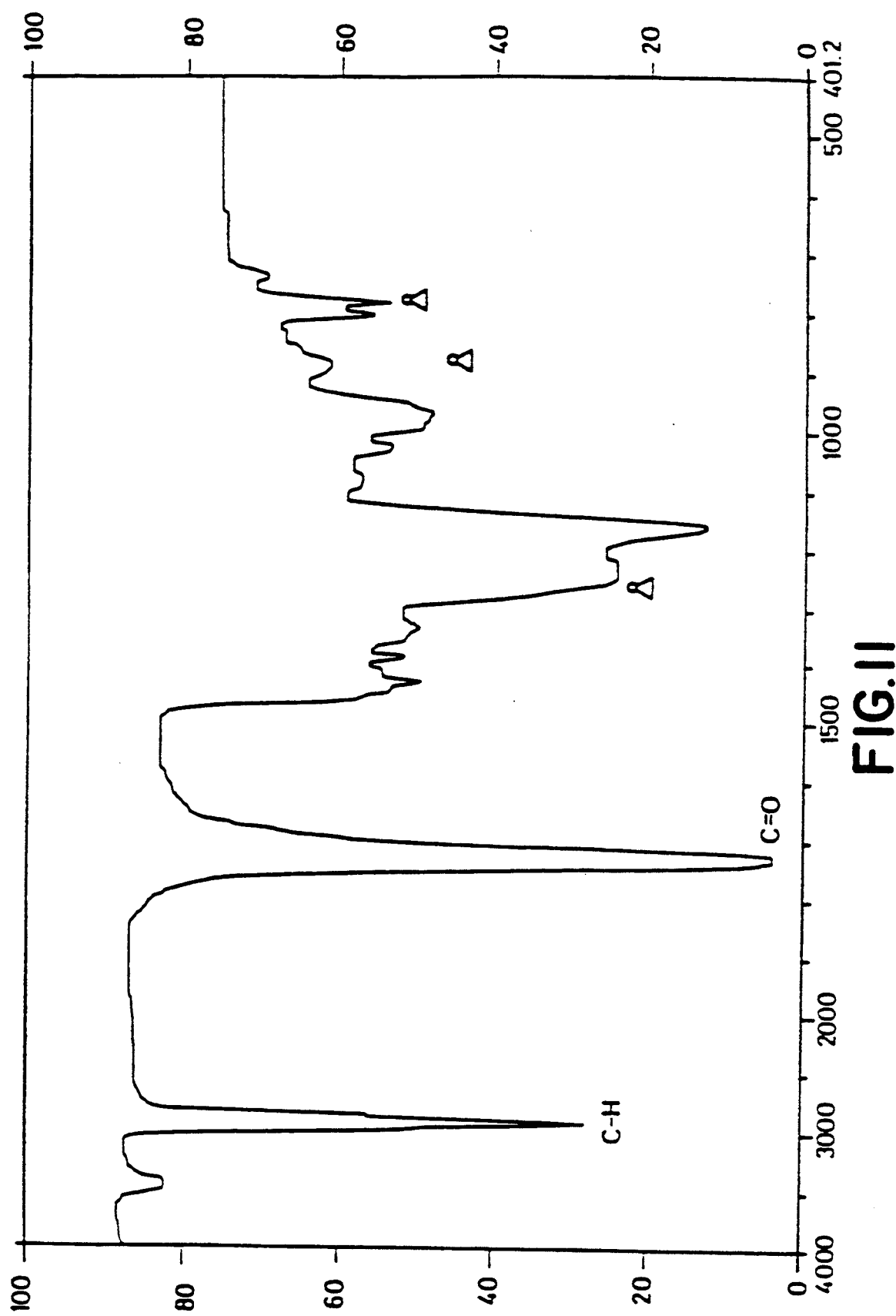
FIG. 11 is an IR spectrum chart and FIG. 12 is a GPC chart relating to a composition obtained in Example 4, respectively.

In the IR chart(FIG. 11), an absorption peak was observed at 1,727 cm$^{-1}$, which is derived from carbonyl group, and absorption peaks were observed at 1,250 cm$^{-1}$, 894 cm$^{-1}$ and 785 cm$^{-1}$, which are derived from the epoxy ring.

Figure 12:
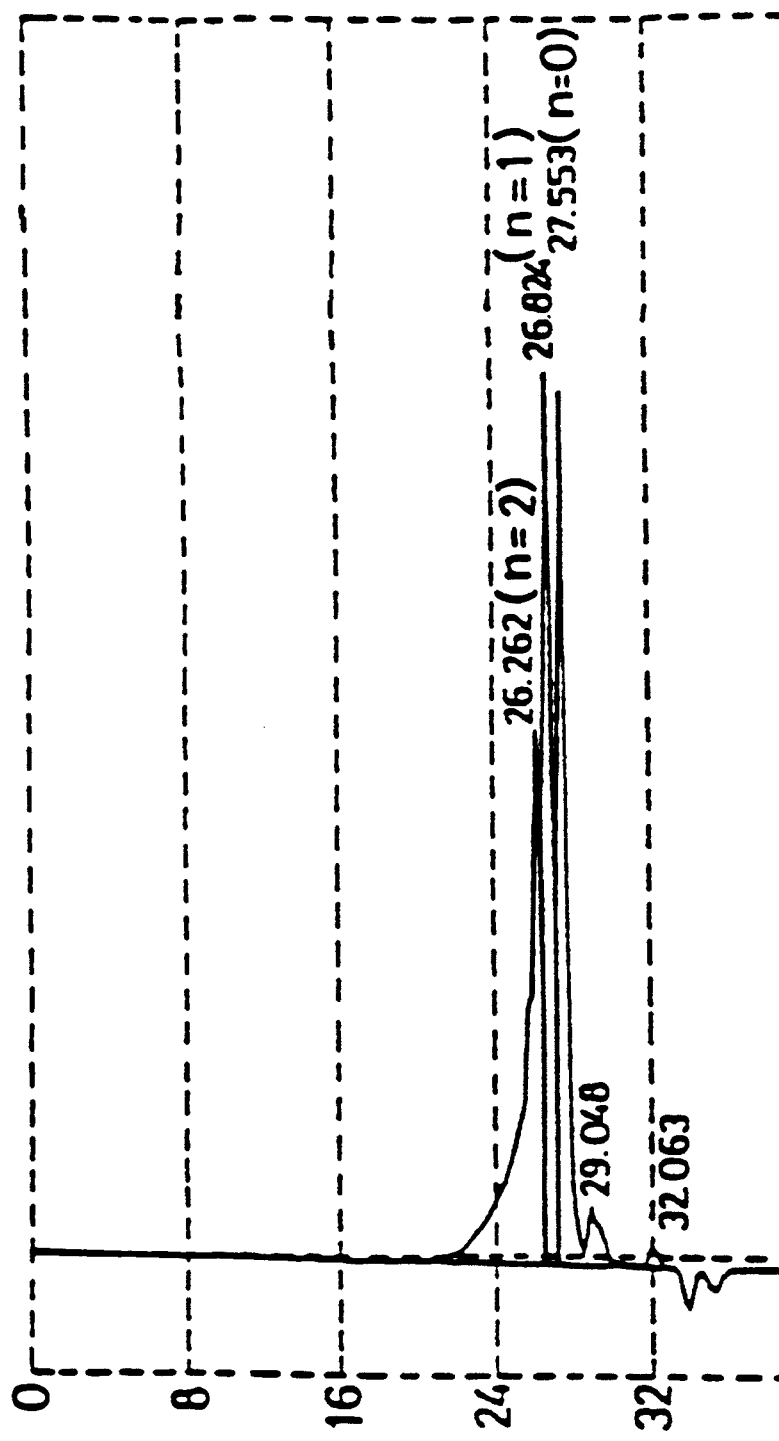

Furthermore, the GPC chart (FIG. 12) illustrates that the product is a mixture composed of a compound into which no epsilon-caprolactone derived ester-bonding units is introduced(n=0), a compound into which one mol of epsilon-caprolactone derived ester-bonding units is introduced(n=1), and compounds which have a distribution(n=2,3,4, ...) of more than 1 mol of epsilon-caprolactone.

It was confirmed that the product is represented by the general formula described hereinafter by the above analyses;

CH$_2$—CO[—O—(CH$_2$)$_5$—CO—]$_{n1}$—O—CH$_2$—Y$^2$
|
CH—CO[—O—(CH$_2$)$_5$—CO—]$_{n2}$—O—CH$_2$—Y$^2$
|
CH—CO[—O—(CH$_2$)$_5$—CO—]$_{n3}$—O—CH$_2$—Y$^2$
|
CH$_2$—CO[—O—(CH$_2$)$_5$—CO—]$_{n4}$—O—CH$_2$—Y$^2$

[wherein Y$^2$ represents

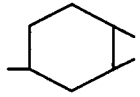 O, n1 + n2 + n3 + n4 = 1].

EXAMPLE 5

A jacketed-reaction vessel equipped with a reflux condenser, an inlet for supplying peracetic acid and a tube for supplying nitrogen gas was charged with 1,000 g. of the product obtained in Example 3 and 1,000 g. of ethyl acetate.

Subsequently, 1.2 g. of 2-ethylhexyl sodium tripolyphosphate was dissolved as a stabilizer into 1,216 g. of ethyl acetate solution containing 30% of peracetic acid.

The peracetic acid and ethyl acetate solution of the stabilizer was added into the ethyl acetate containing peracetic acid and the product in Example 3 while maintaining a reaction temperature of 40° C. over approximately 3 hours.

Further reaction temperature of 40° C. was maintained over approximately 3 hours.

Successively, 3,200 g. of pure water was added to the solution.

After stirring for 30 minutes, the solution was allowed to stand without stirring at the temperature of 40° C. to separate into two liquid layers. After 30 minutes, the lower liquid layer was gradually removed from upper liquid.

Successively, 1,500 g. of ethyl acetate was added into the upper liquid, and then 3,200 g. of pure water was added, followed by stirring for 30 minutes and settled at the temperature of 40° C. for 30 minutes in order to remove a resulting lower layer.

In addition, 3,200 g. of pure water was added into the upper liquid layer and stirred at a temperature of 40° C. for 30 minutes and allowed to settle in order to remove a resulting llower layer.

The upper liquid layer obtained was supplied into a thin-film evaporator maintained at a temperature of 120° C. and a pressure reduction degree of 50 mm Hg, with supplying speed of 300 cc/hour to obtain 1,050 g. of a product.

The product exhibited the properties described hereinafter.

| | |
|---|---|
| Color hue (APHA) | 30 |
| Oxirane oxygen concentration (%) | 6.2 |
| Acid value (mg KOH/g) | 0.5 |
| Viscosity (cp/70° C.) | 1,000 |

Then, the product obtained was analyzed with a $^1$H-NMR, an IR spectrometer to obtain the following results.

Figure 13:
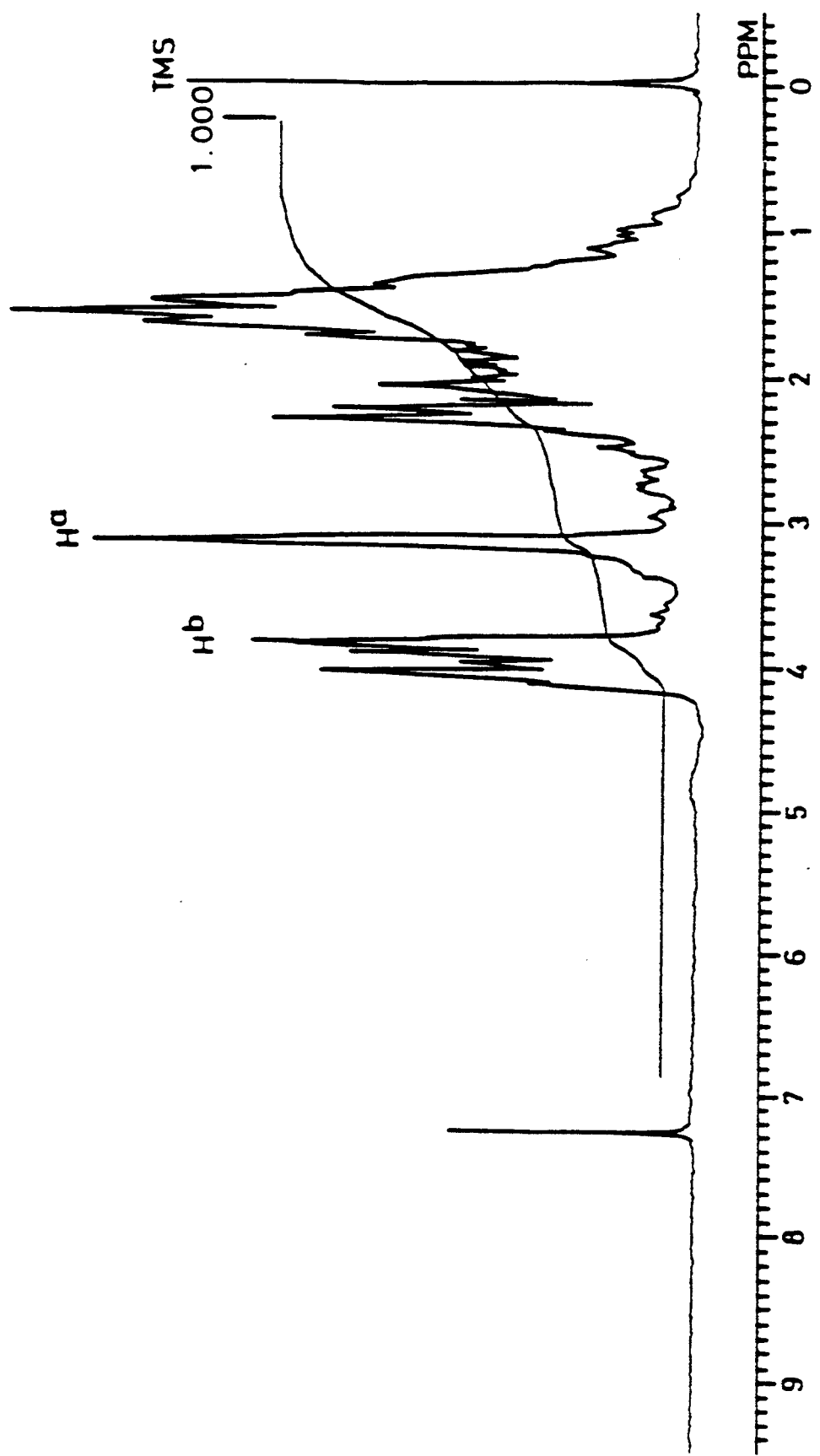
FIG. 13 is $^1$H-NMR chart.

In the NMR spectrum chart(FIG. 13), a multiplet delta 3.1 is to 3.3(H$^a$) is derived from a methylene hydrogen in epoxy ring, and a multiplet delta 3.8 to 4.2(H$^b$) is derived from a hydrogen of the methylene group which is adjacent to oxygen atom.

Figure 14:
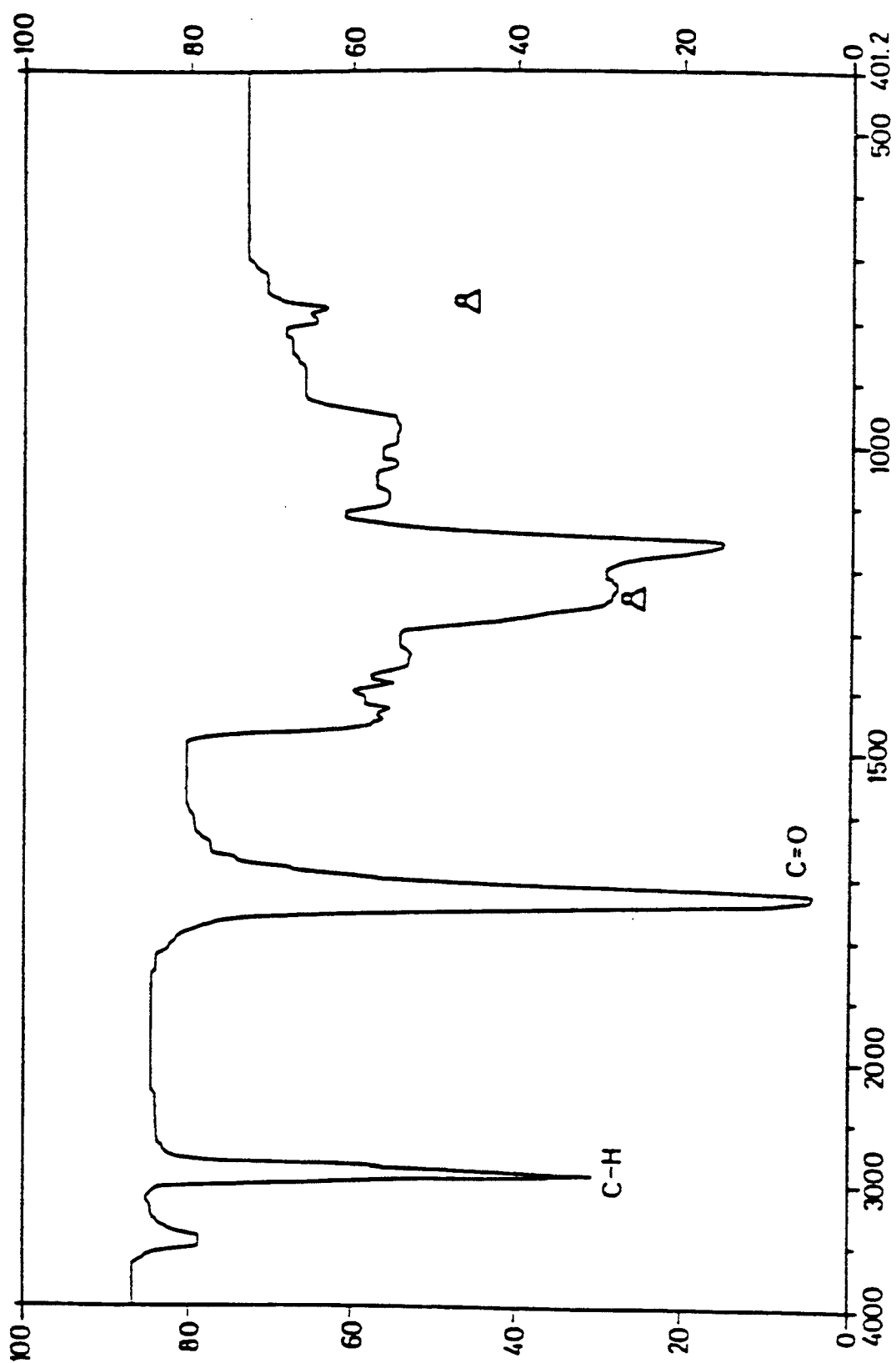
FIG. 14 is an IR spectrum chart and FIG. 15 is a GPC chart relating to a composition obtained in Example 5, respectively.

In the IR chart(FIG. 14), an absorption peak was observed at 1,728 cm$^{-1}$, which is derived from carbonyl group, and absorption peaks were observed at 1,231 cm$^{-1}$ and 784 cm$^{-1}$, which are derived from epoxy ring.

Figure 15:
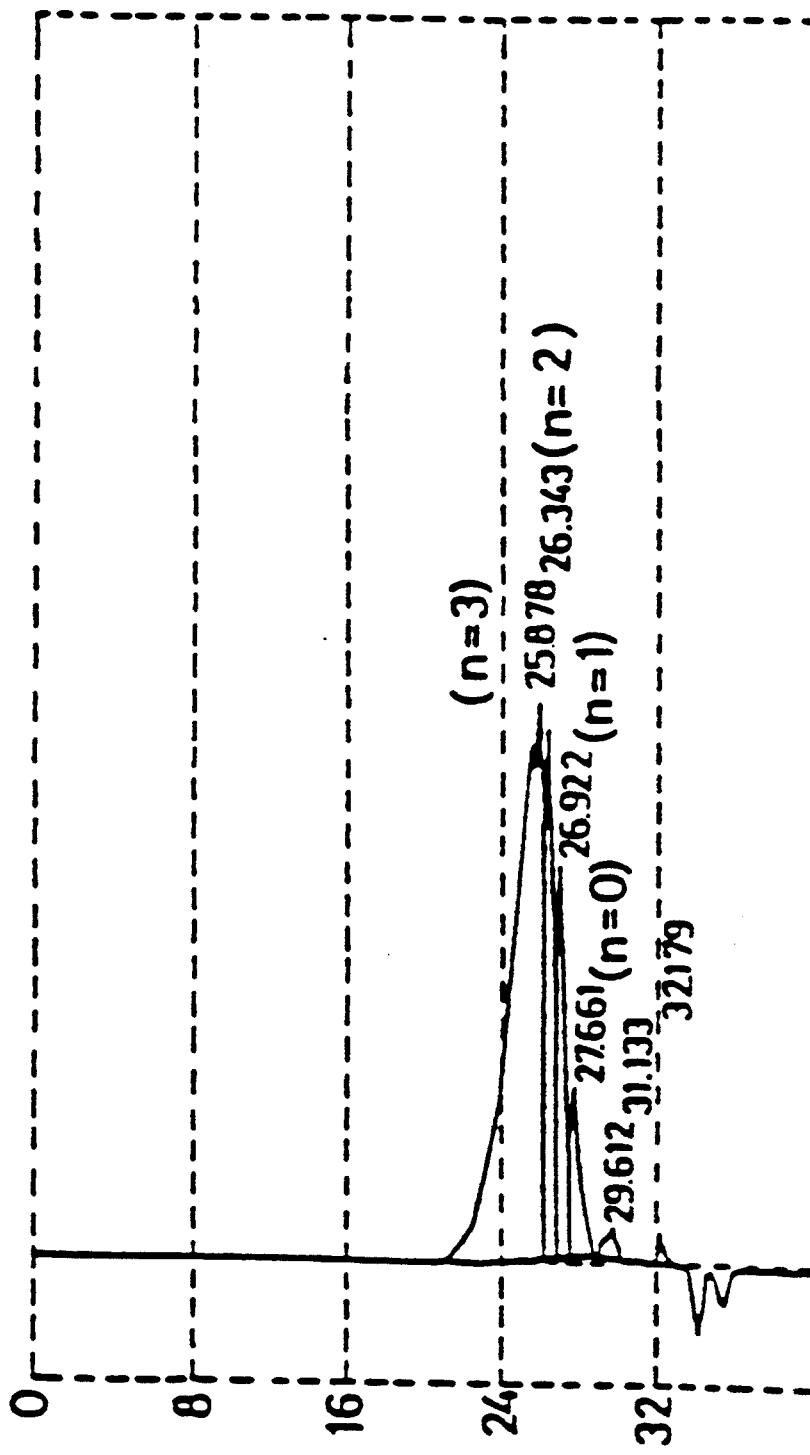

Furthermore, the GPC chart (FIG. 15) illustrates that the product is a mixture composed of a compound into which no epsilon-caprolactone derived ester-bonding units is introduced(n=0), a compound into which one mol of epsilon-caprolactone derived ester-bonding unit is introduced(n=1), and compounds which have a distribution(n=2,3,4, ...) of more than 1 mol of epsilon-caprolactone derived ester-bonding unit.

It was confirmed that the product is represented by the general formula described hereinafter by the above analyses;

CH$_2$—CO[—O—(CH$_2$)$_5$—CO—]$_{n1}$—O—CH$_2$—Y$^2$
|
CH—CO[—O—(CH$_2$)$_5$—CO—]$_{n2}$—O—CH$_2$—Y$^2$
|
CH—CO[—O—(CH$_2$)$_5$—CO—]$_{n3}$—O—CH$_2$—Y$^2$
|
CH$_2$—CO[—O—(CH$_2$)$_5$—CO—]$_{n4}$—O—CH$_2$—Y$^2$

[wherein Y$^2$ represents

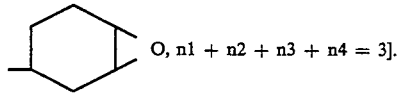 O, n1 + n2 + n3 + n4 = 3].

SYNTHESIS EXAMPLE 4

The same procedures described as in Synthesis Example 1 were repeated, except that 991.0 g. of 3-cyclohexene 1-methanol, 800 g. of epsilon-caprolactone and 206 g. of beta-methyl-delta varelolactone were used.

It was confirmed by gas chromatography analysis that 0.3% of unreacted epsilon-caprolactone and 5.0% of beta-methyl-delta varelolactone remained.

The lactones remaining were removed by distillation under a pressure remaining of 5 mm Hg and a temperature of 120° C. to obtain a composition having 0.1% of epsilon-caprolactone and 0.9% of beta-methyl-delta varelolactone remaining.

SYNTHESIS EXAMPLE 5

The same procedures described as in Synthesis Example 1 were repeated, except that 991.0 g. of 3-cyclohexene 1-methanol, 800 g. of epsilon-caprolactone and 281.9 g. of trimethylcaprolactone were used.

It was confirmed by gas chromatography analysis that 0.4% of unreacted epsilon-caprolactone and 4.0% of trimethylcaprolactone remained.

The remaining lactones were removed by distillation under a reduced pressure of 5 mm Hg and a temperature of 120° C. to obtain a composition having 0.1% of epsilon-caprolactone and 0.3% of trimethylcapolactone remaining.

EXAMPLE 6

The same procedures described as in Example 1 were repeated, except that 587.7 g. of butanetetracarboxylic acid, 420 g. of 3-cyclohexene 1-methanol, 570 g. of the composition obtained in Synthesis Example 4 were used.

The contents in the reaction vessel were gradually raised to a temperature of 150° C. over 1 hour, as a result, the contents became roughly homogeneous, followed by initiation of water distillation.

Additionally, the reaction temperature was raised to 220° C. over approximately 3 hours, and further reaction was continued for approximately 37 hours.

Subsequently, the contents were cooled to a temperature of 140° C., and then excess 3-cyclohexene 1-methanol was distilled out of the reaction system under a reduced pressure of from 1 to 10 mm Hg, to obtain 1,524 g. of a product.

It was confirmed by gas chromatography analysis that unreacted 3-cyclohexene 1-methanol was less than 0.1%.

Furthermore, it was confirmed that the esterification reaction was almost completed, because an acid value of the product was reduced to 0.90.

EXAMPLE 7

The same procedures described as in Example 1 were repeated, except that 580.0 g. of butanetetracarboxylic acid, 418 g. of 3-cyclohexene 1-methanol and 560.0 g. of the composition obtained in Synthesis Example 5 were used.

The contents in the reaction vessel were gradually raised to a temperature of 150° C. over 1 hour, as a result, the contents became roughly homogeneous, followed by initiation of water distillation.

Additionally, the reaction temperature was raised to 220° C. over approximately 3 hours, and further reaction was continued for approximately 37 hours.

Subsequently, the contents were cooled to a temperature of 140° C., and then excess 3-cyclohexene 1-methanol was distilled out of the reaction system under a reduced pressure reduction ranging from 1 to 10 mm Hg, to obtain 1,510 g. of a product.

It was confirmed by gas chromatography analysis that unreacted 3-cyclohexene 1-methanol was less than 0.1%.

EXAMPLE 8

A jacketed-reaction vessel equipped with a reflux condenser, a funnel for dropwise addition and a tube for supplying nitrogen gas was charged with 724.0 g. of the product obtained in Example 6 and 201 g. of ethyl acetate.

Subsequently, 0.3 g. of 2-ethylhexyl sodium triphosphate was dissolved as a stabilizer into 303.0 g. of ethyl acetate solution containing 30% of acetic acid, in the funnel.

The peracetic acid and ethyl acetate solution containing the stabilizer was added into the ethyl acetate solution containing peracetic acid and the product obtained in Example 6 while keeping the reaction temperature of 40° C. over approximately 3 hours.

Also the reaction temperature of 40° C. was kept for approximately 2 hours.

Successively, 1,100 g. of pure water was added to the solution.

After stirring for 30 minutes, the solution was allowed to stand without stirring at the temperature of 40° C. to separate it into two liquid layers. After 30 minutes, the lower liquid layer was gradually removed from upper liquid.

Successively, 1,100 g. of pure water was added into the upper liquid, followed by stirring for 30 minutes and allowed to settle at the temperature of 40° C. for 30 minutes to remove a resulting lower layer.

The upper liquid layer obtained was fed into a thin-film evaporator maintained at the temperature of 120° C. and a reduced pressured degree of 50 mm Hg, with feeding speed of 300 cc/hour to obtain 725 g. of a product.

The product exhibited the properties described hereinafter.

| | |
|---|---|
| Color hue (APHA) | 50 |
| Oxirane oxygen concentration (%) | 9.8 |
| Acid value (mg KOH/g) | 0.9 |
| Viscosity (cp/70° C.) | 7,000 |

The product was liquid at ordinary temperatures.

EXAMPLE 9

A jacketed-reaction vessel equipped with a reflux condenser, a funnel for dropwise addition and a tube for supplying nitrogen gas was charged with 724 g. of the product obtained in Example 7 and 201 g. of ethyl acetate.

Subsequently, 0.3 g. of ethylhexyl sodium tripolyphosphate was dissolved as a stabilizer into 303.0 g. of ethyl acetate solution containing 30% of peracetic acid in the funnel.

The peracetic acid and ethyl acetate solution of the stabilizer was added dropwise into the ethyl acetate solution containing peracetic acid and the product in Example 7 while keeping a reaction temperature of 40° C. for approximately 3 hours.

Further reaction temperature of 40° C. was kept for over approximately 2 hours.

Subsequently, 1,100 g. of pure water was added to the solution.

After stirring for 30 minutes, the solution was allowed to stand without stirring at the temperature of 40° C. to separate into two liquid layers. After 30 minutes, the lower liquid layer was gradually removed from upper liquid.

Subsequently, 300 g. of ethyl acetate and 1,100 g. of pure water were added into the upper liquid, and then 3,200 g. of pure water was added, followed by stirring for 30 minutes and the mixture was allowed to settle at the temperature of 40° C. for 30 minutes to remove a resulting lower layer.

The upper liquid layer obtained was supplied into a thin-film evaporator maintained at the temperature of 120° C. and a reduced pressure of 50 mm Hg, with feeding speed of 300 cc/hour to obtain 720 g. of a product.

The product exhibited the properties described hereinafter.

| | |
|---|---|
| Color hue (APHA) | 60 |
| Oxirane oxygen concentration (%) | 9.3 |
| Acid value (mg KOH/g) | 9.3 |
| Viscosity (cp/70° C.) | 7,000 |

The product was liquid at ordinary temperatures.

EXAMPLE 10

A reaction vessel equipped with a stirrer and a tube for distilling water was charged with 1,400 g. of tetrahydrophthalic anhydride, 2,267 g. of 3-cyclohexene 1-methanol and 1,566 g. of the product obtained in Synthesis Example 2.

The contents in the reaction vessel were gradually raised to a temperature of 150° C. over 3 hour, as a result, the contents became roughly homogeneous, and water distillation was started.

Additionally, the reaction temperature was raised to 220° C. over approximately 3 hours, and further reaction was continued for approximately 50 hours.

Subsequently, the contents yore cooled to a temperature of 140° C., and then the excess 3-cyclohexene 1-methanol was distilled out of the reaction system under a reduced pressure ranging from 1 to 10 mm Hg, to obtain a product having an acid value of 2.90, a viscosity (cp/45° C.) of 107 and a viscosity (cp/25° C.) of 429.

Figure 16:
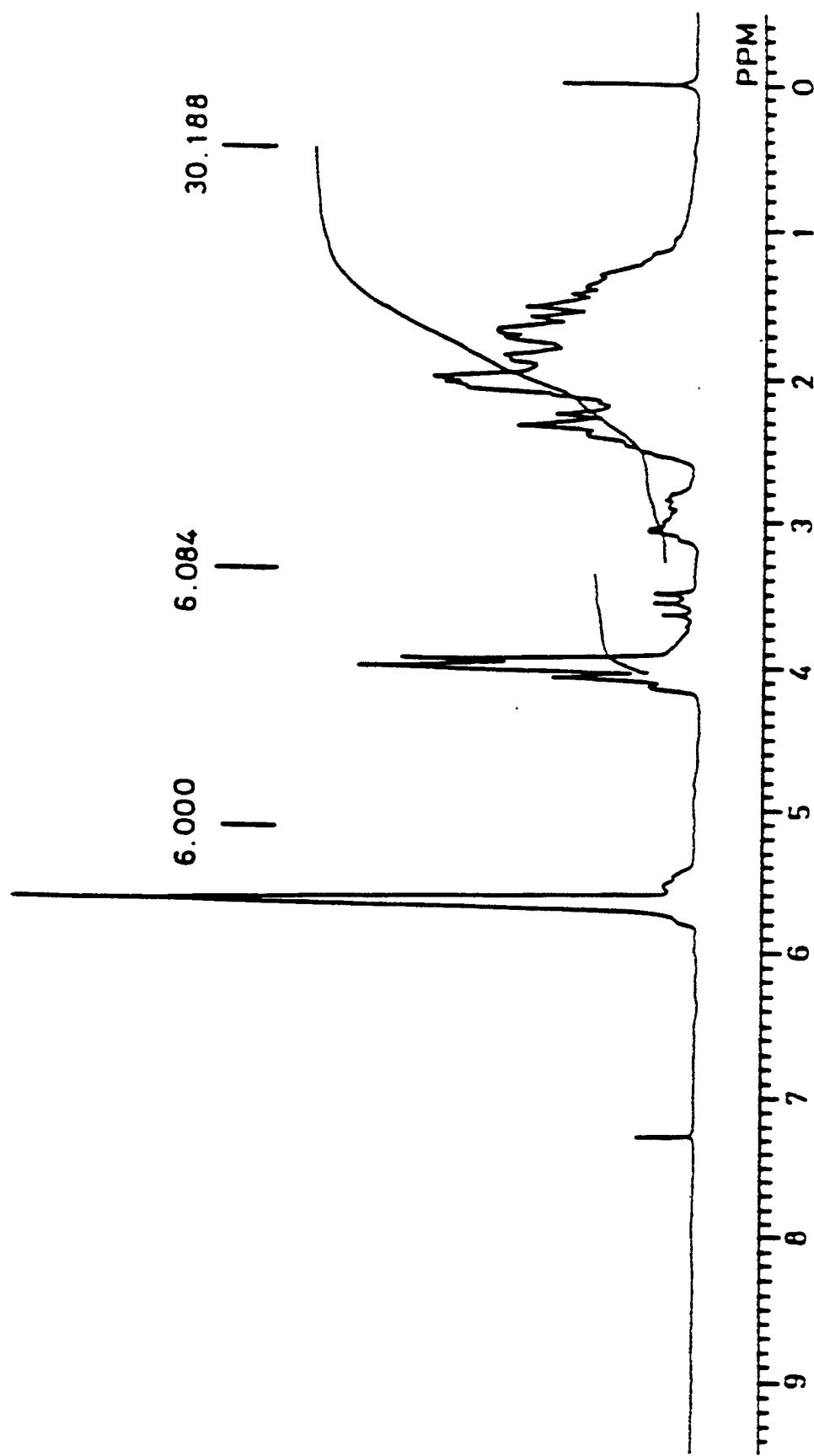
FIG. 16 is $^1$H-NMR chart.
Figure 17:
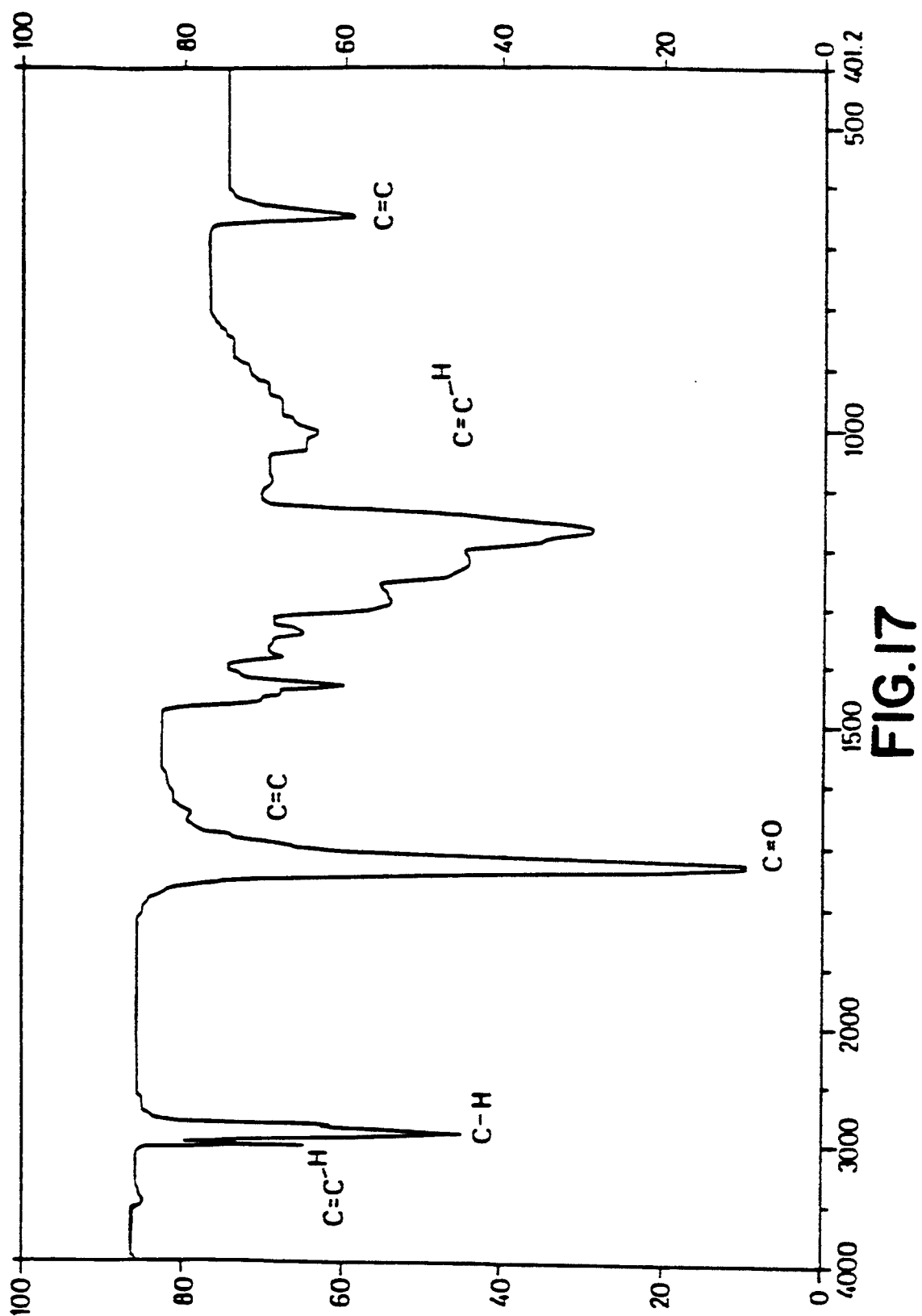
FIG. 17 is an IR spectrum chart and FIG. 18 is a GPC chart relating to a composition obtained in Example 10, respectively.

Successively, the product obtained was analyzed with a $^1$H-NMR equipment and an IR spectrometer. The spectra are shorn in FIG. 16 and FIG. 17, respectively.

In the $^1$H-NMR spectrum chart(FIG. 16), a singlet delta 5.67($H^a$) is derived from a methylene hydrogen of epoxy ring. and a multiplet delta 3.9 to 4.2($H^b$,$H^c$) is derived from a hydrogen of the methylene group which is adjacent to an oxygen atom.

It is noted that a signal due to acid proton was not observed.

In the IR spectrum chart(FIG. 17), an absorption peak was observed at 1730 cm$^{-1}$, which is derived from carbonyl group, absorption peaks were observed at 3,090 cm$^{-1}$, 1,647 cm$^{-1}$, 1,012 cm$^{-1}$ and 653 cm$^{-1}$, which are derived from double bonds.

An absorption peak around 3,500 cm$^{-1}$, which peak is derived from hydroxyl group was found to have disappeared.

Figure 18:
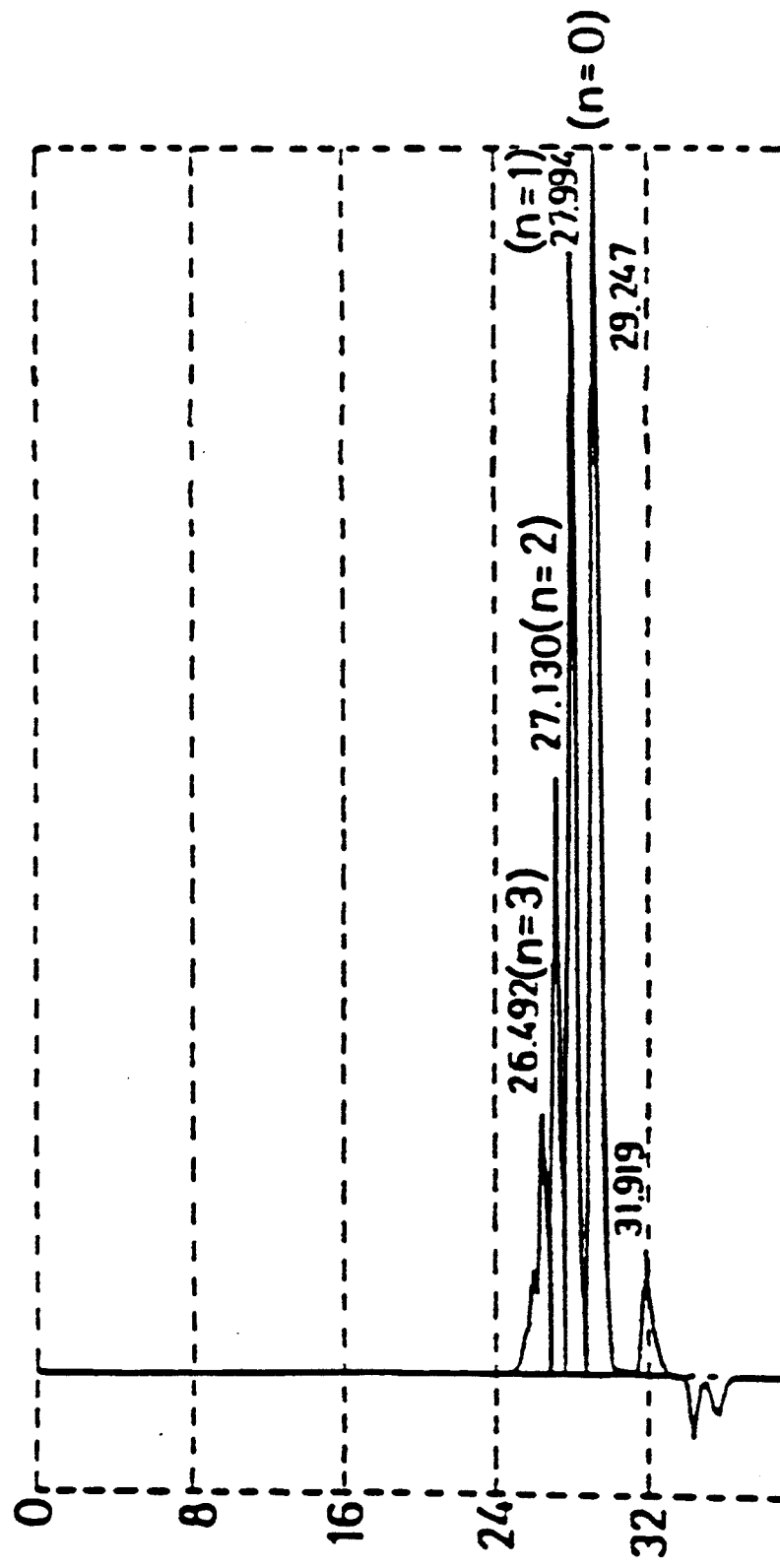

Furthermore, the GPC chart (FIG. 18) illustrates that the product is a mixture composed of a compound into which no epsilon-caprolactone derived ester-bonding unit is introduced(n=0), a compound into which one mol of epsilon-caprolactone derived ester-bonding unit is introduced(n=1), and compounds which have a distribution(n=2,3,4, ...) of more than 1mol of epsilon-caprolactone derived ester-bonding unit.

It was confirmed that the product is represented by the general formula described hereinafter by the above analyses;

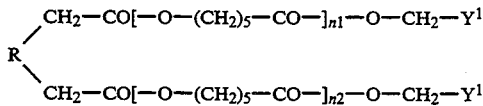

[wherein $Y^1$ represents

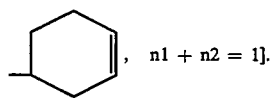, n1 + n2 = 1].

EXAMPLE 11

The same procedures described as in Example 12 were repeated, except that 1,141 g. of tetrahphthalic anhydride, 1,431 g. of 3-cyclohexene 1-methanol and 2,554 g. of the composition obtained in Synthesis Example 2 were used to obtain a product having an acid value of 1.0, a viscosity (cp/45° C.) of 92 and a viscosity (cp/25° C.) of 303.

Figure 19:
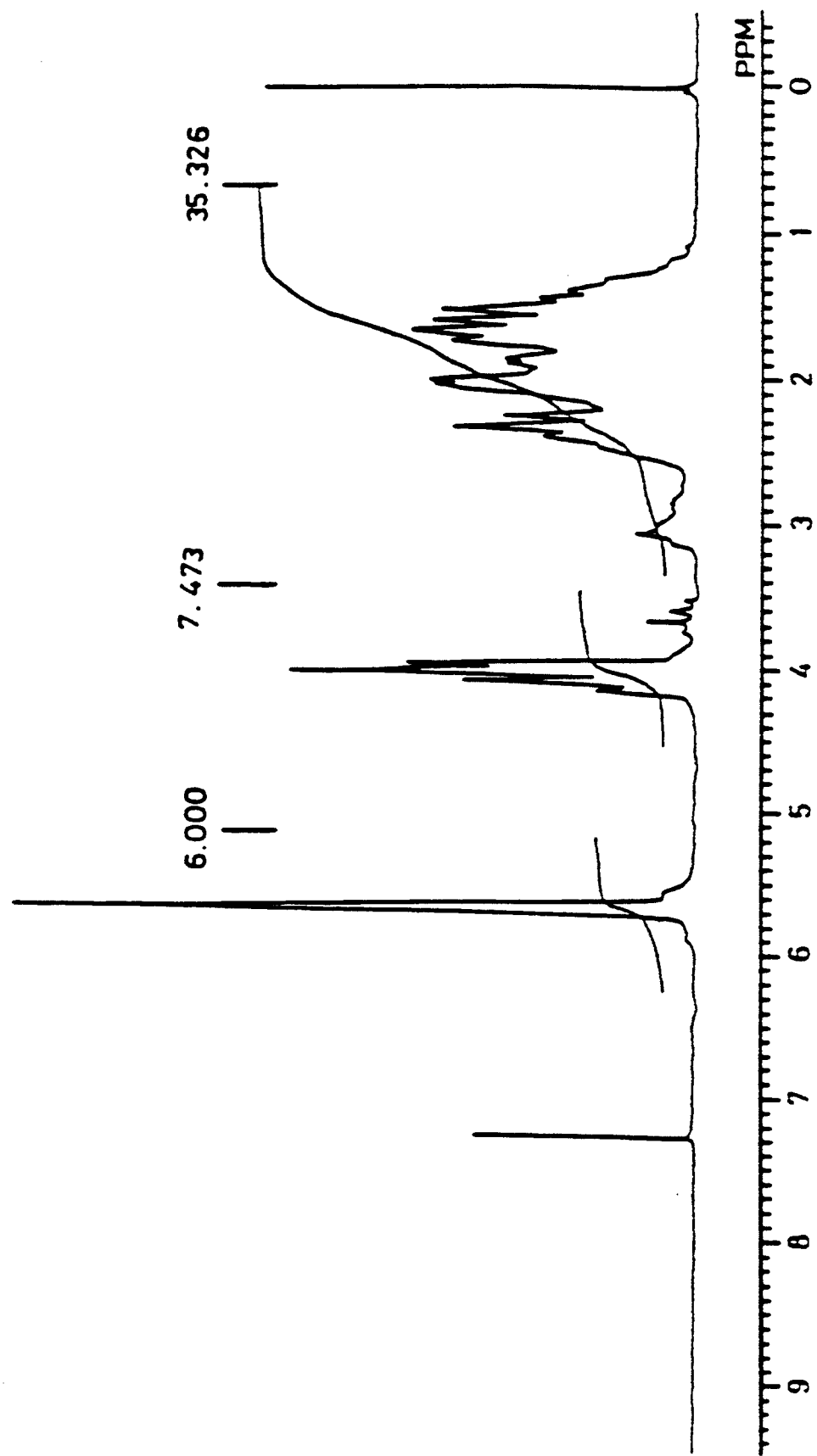
FIG. 19 is $^1$H-NMR chart.
Figure 20:
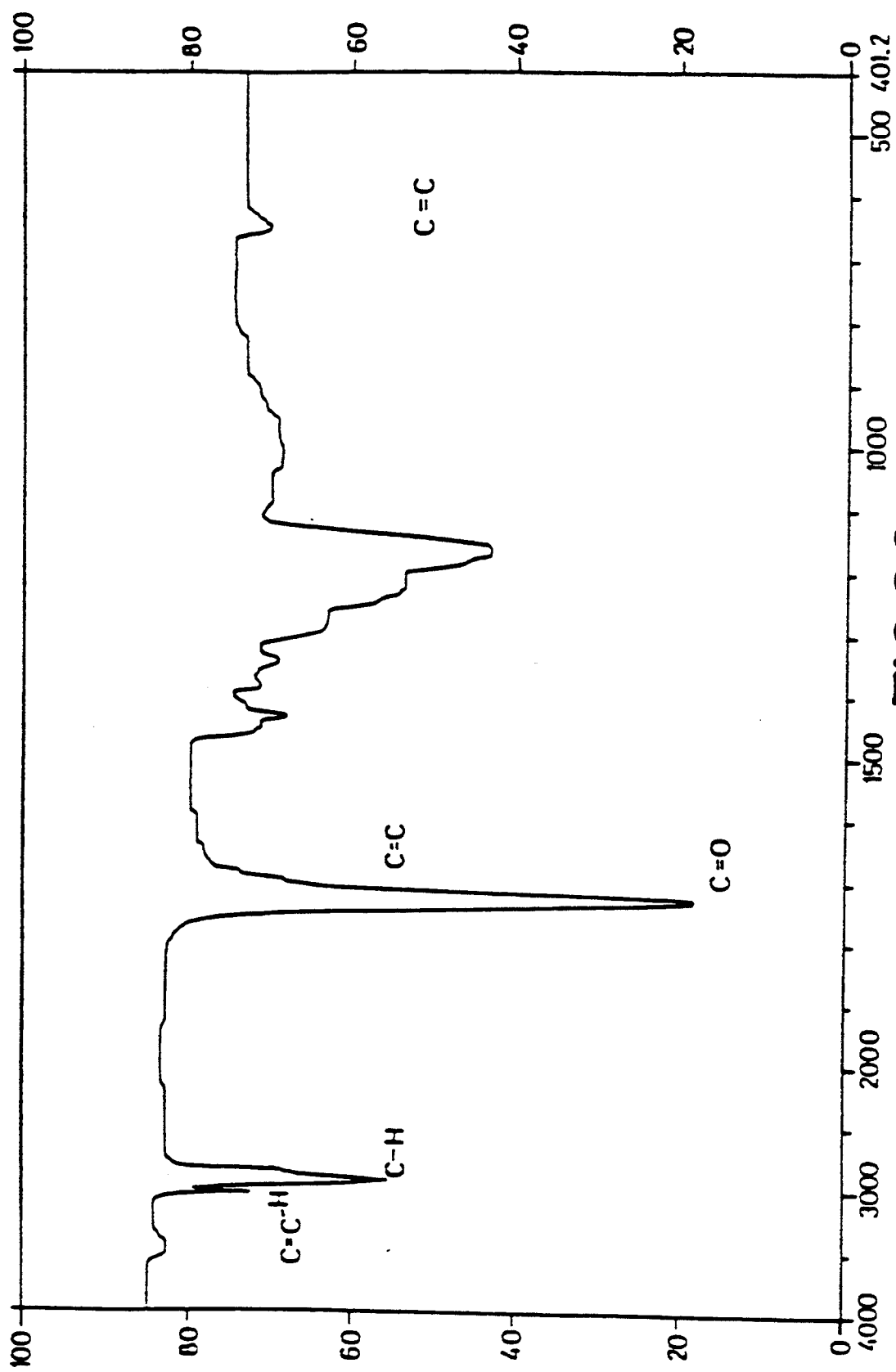
FIG. 20 is an IR spectrum chart and FIG. 21 is a GPC chart relating to a composition obtained in Example 11, respectively.

Subsequently, the product obtained was analyzed with a $^1$H-NMR equipment and an IR spectrometer. The spectra are shown in FIG. 19 and FIG. 20, respectively.

In the $^1$H-NMR spectrum chart(FIG. 19), a singlet delta 5.67($H^a$) is derived from a methylene hydrogen of epoxy ring, and a multiplet delta 3.9 to 4.2($H^b$,$H^c$) is derived from a hydrogen of the methylene group which is adjacent to an oxygen atom.

No signal due to acid proton was observed.

In the IR spectrum chart(FIG. 20), an absorption peak was observed at 1,730 cm$^{-1}$, which is derived from carbonyl group, absorption peaks were observed at 3,140 cm$^{-1}$, 1,683 cm$^{-1}$ and 652 cm$^{-1}$, which are derived from double bonds.

An absorption peak around 3,500 cm$^{-1}$ is derived from hydroxyl group was found to have disappeared.

Figure 21:
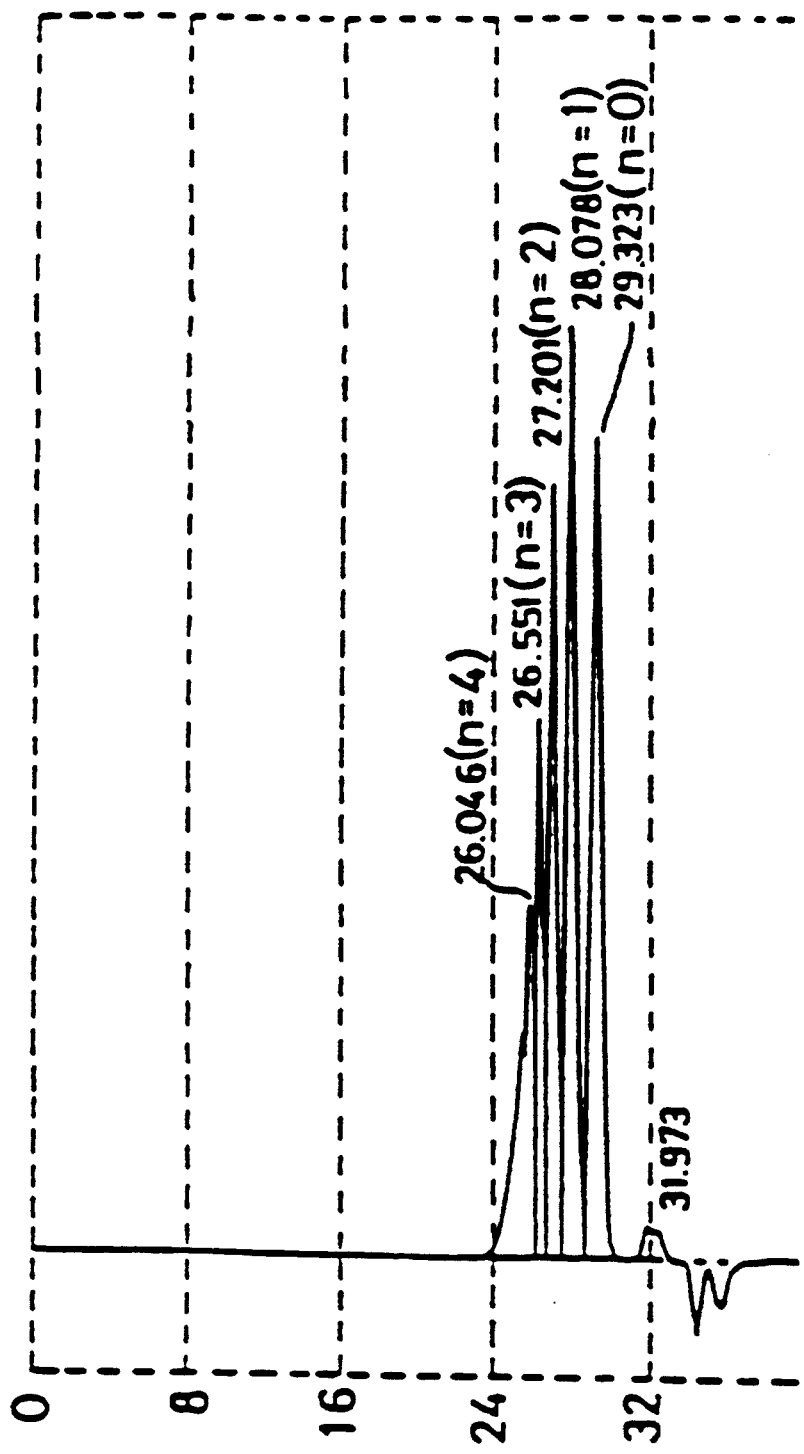

Furthermore, the GPC chart (FIG. 21) illustrates that the product is a mixture composed of a compound into which no epsilon-caprolactone derived ester-bonding unit is introduced(n=0), a compound into which one mol of epsilon-caprolactone derived ester-bonding unit is introduced(n=1), and compounds which have a distribution(n=2,3,4, ...) of more than 1 mol of epsilon-caprolactone derived ester-bonding unit.

It was confirmed that the product is represented by the general formula described hereinafter by the above analyses;

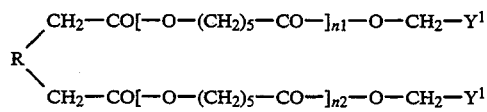

[wherein $Y^1$ represents

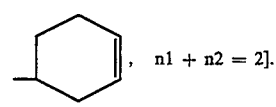, n1 + n2 = 2].

EXAMPLE 12

A jacketed-reaction vessel equipped with a reflux condenser, an inlet for supplying peracetic acid and a tube for supplying nitrogen gas was charged with 770.6 g. of the product obtained in Example 10.

Successively, 2.9 g. of potassium pyrophosphate was dissolved as a stabilizer into 1,459 g. of ethyl acetate solution containing 30% of peracetic acid.

The peracetic acid and ethyl acetate solution of the stabilizer was added into the ethyl acetate solution containing peracetic acid and the product in Example 10 while maintaining a reaction temperature of 40° C. over approximately 3 hours.

Further reaction temperature of 40° C. was kept for approximately 3 hours.

Subsequently, 1,100 g. of peracetic acid and 2,500 g. of pure water were added into the solution.

After stirring for 30 minutes, the solution was allowed to stand without stirring at the temperature of 40° C. to separate into two liquid layers. After 30 minutes, the lower liquid layer was gradually removed from upper liquid.

Subsequently, 2,500 g. of pure water was added into the upper liquid, and then stirred for 30 minutes and allowed to settle at the temperature of 40° C. for 30 minutes to remove a resulting lower liquid.

The same separation processes were repeated twice.

The upper liquid layer obtained was supplied into a thin-film evaporator kept at the temperature of 120° C. and a reduced pressure of 50 mm Hg, with feeding speed of 300 cc/hour to obtain 780 g. of a product.

The product exhibited the properties described hereinafter.

| Color hue (APHA) | 30 |
| Oxirane oxygen concentration (%) | 8.0 |
| Acid value (mg KOH/g) | 1.0 |

Subsequently, the product obtained was analyzed with a GPC equipment, a $^1$H-NMR equipment and an IR spectrometer to obtain the following results.

In the $^1$H-NMR spectrum chart(FIG. 21), a multiplet delta 3.0 to 3.3($H^a$) is derived from a methylene hydrogen of epoxy ring, and a multiplet delta 3.8 to 4.2($H^b$,$H^c$) is derived from a hydrogen of the methylene group which is adjacent to oxygen atom.

Figure 22:
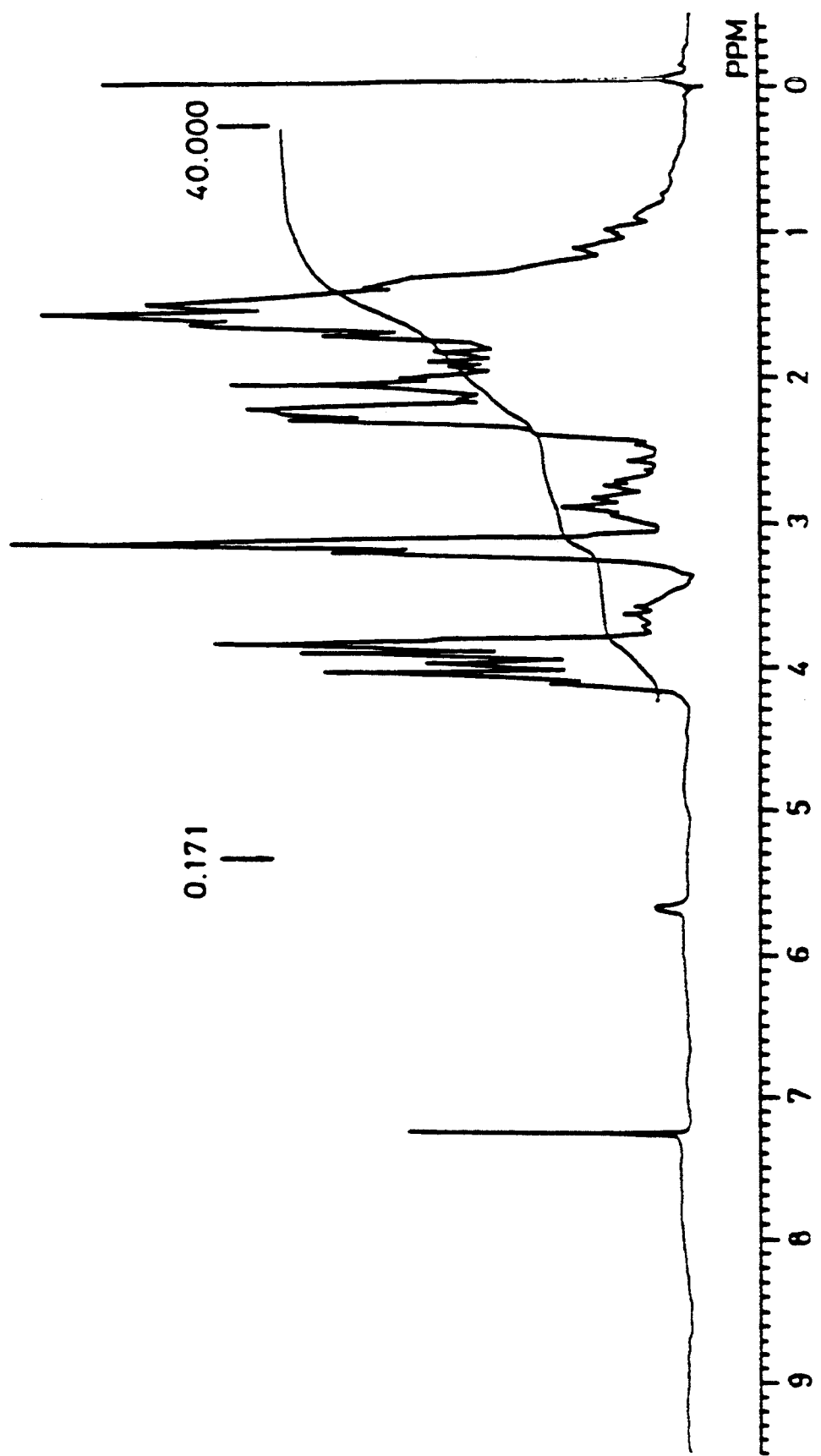
FIG. 22 is $^1$H-NMR chart.

In the IR spectrum chart(FIG. 22), an absorption peak was observed at 1,722 cm$^{-1}$, which is derived from carbonyl group, absorption peaks were observed at 1,250 cm$^{-1}$, 892 cm$^{-1}$ and 784 cm$^{-1}$, which are derived from an epoxy ring.

Figure 23:
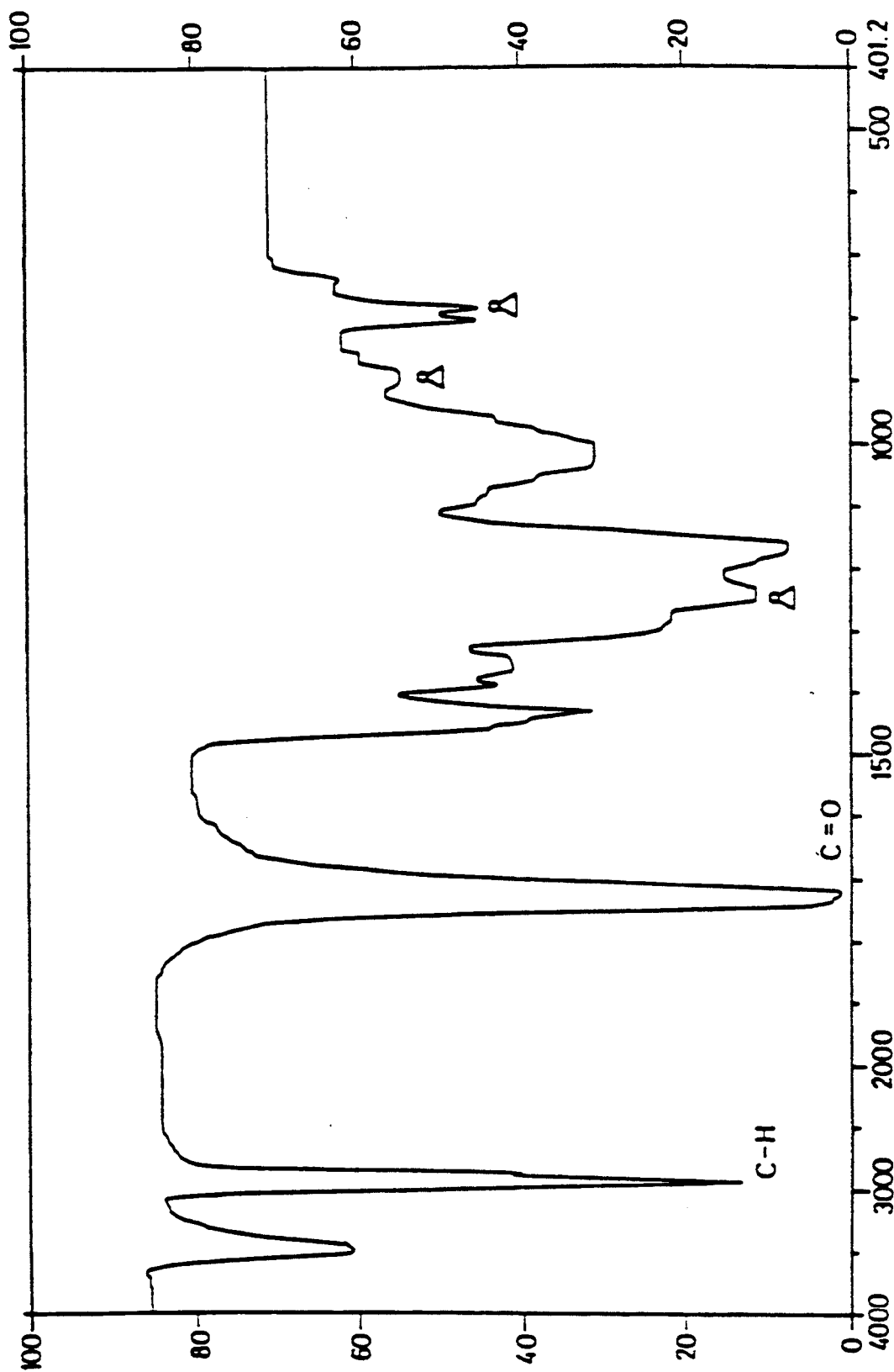
FIG. 23 is an IR spectrum chart and FIG. 24 is a GPC chart relating to a composition obtained in Example 12, respectively.

Furthermore, the GPC chart (FIG. 23) illustrates that the product is a mixture composed of a compound into which no epsilon-caprolactone derived ester-bonding unit is introduced(n=0), a compound into which one mol of epsilon-caprolactone derived ester-bonding unit is introduced(n=1 ), and compounds which have a distribution(n=2,3,4, ... ) of more than 1 mol of epsilon-caprolactone derived ester-bonding unit.

It was confirmed that the product is represented by the general formula described hereinafter by the above analyses;

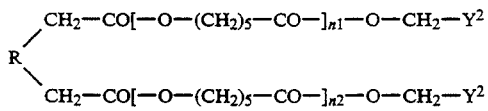

[wherein $Y^2$ represents

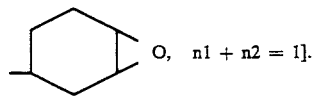

O,  n1 + n2 = 1].

EXAMPLE 13

The same procedures described as in Example 14 were repeated, except that 733.3 g. of the product obtained in Example 11, 1140 g. of peracetic acid and 2.2 g. of potassium pyrophosphate were used to obtain 720 g. of a product having the following properties.

| Color hue (APHA) | 20 |
| Oxirane oxygen concentration (%) | 7.0 |

-continued

| Acid value (mg KOH/g) | 0.9 |
| Viscosity (cp/70° C.) | 302 |

Subsequently, the product obtained was analyzed with a GPC equipment, a $^1$H-NMR equipment and an IR spectrometer to obtain the following results.

Figure 24:
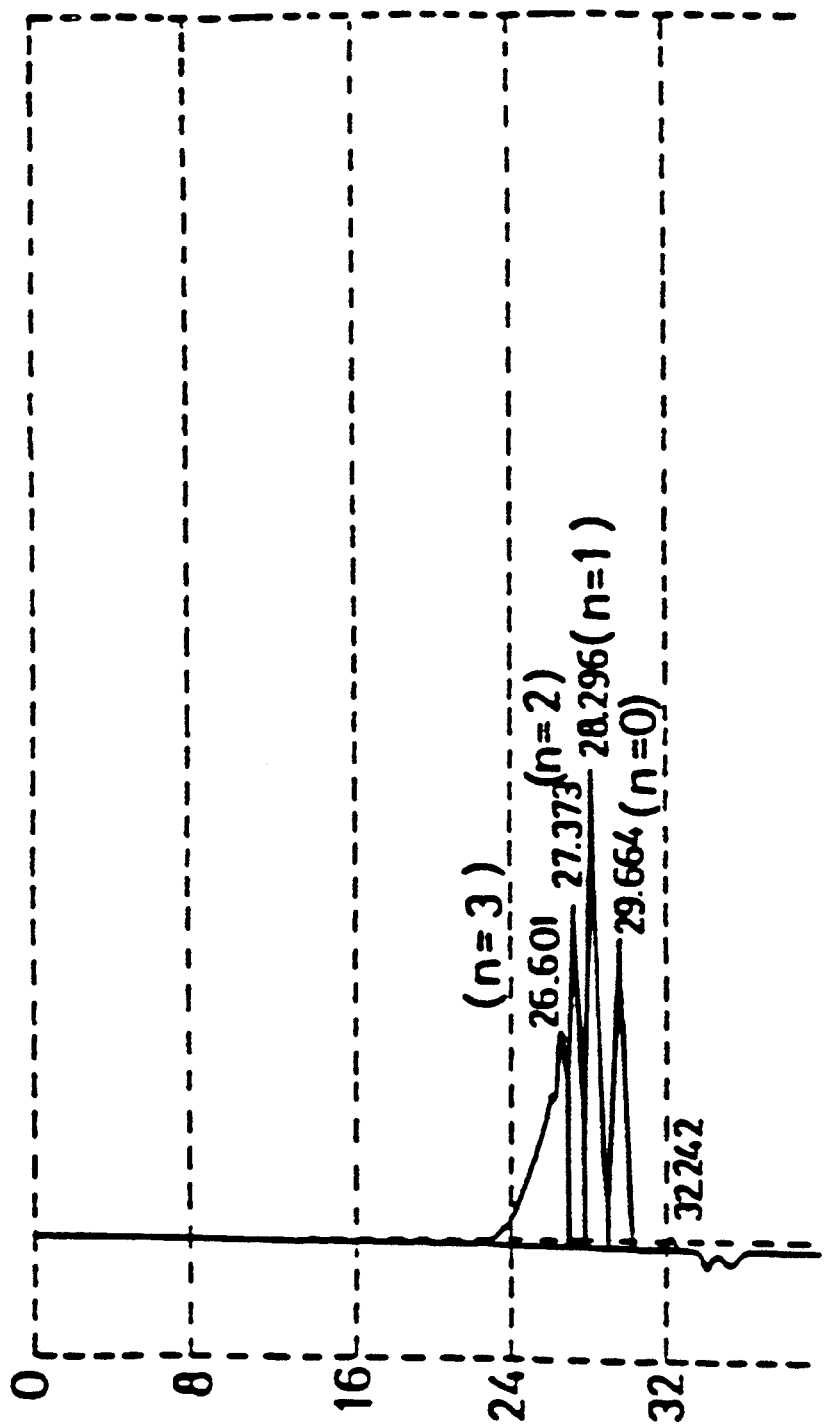

In the $^1$H-NMR spectrum chart(FIG. 24), a multiplet delta 3.0 to 3.3($H^a$) is derived from a methylene hydrogen of epoxy ring, and a multiplet delta 3.8 to 4.2($H^b$,$H^c$) is derived from a hydrogen of the methylene group which is adjacent to oxygen atom.

Figure 25:
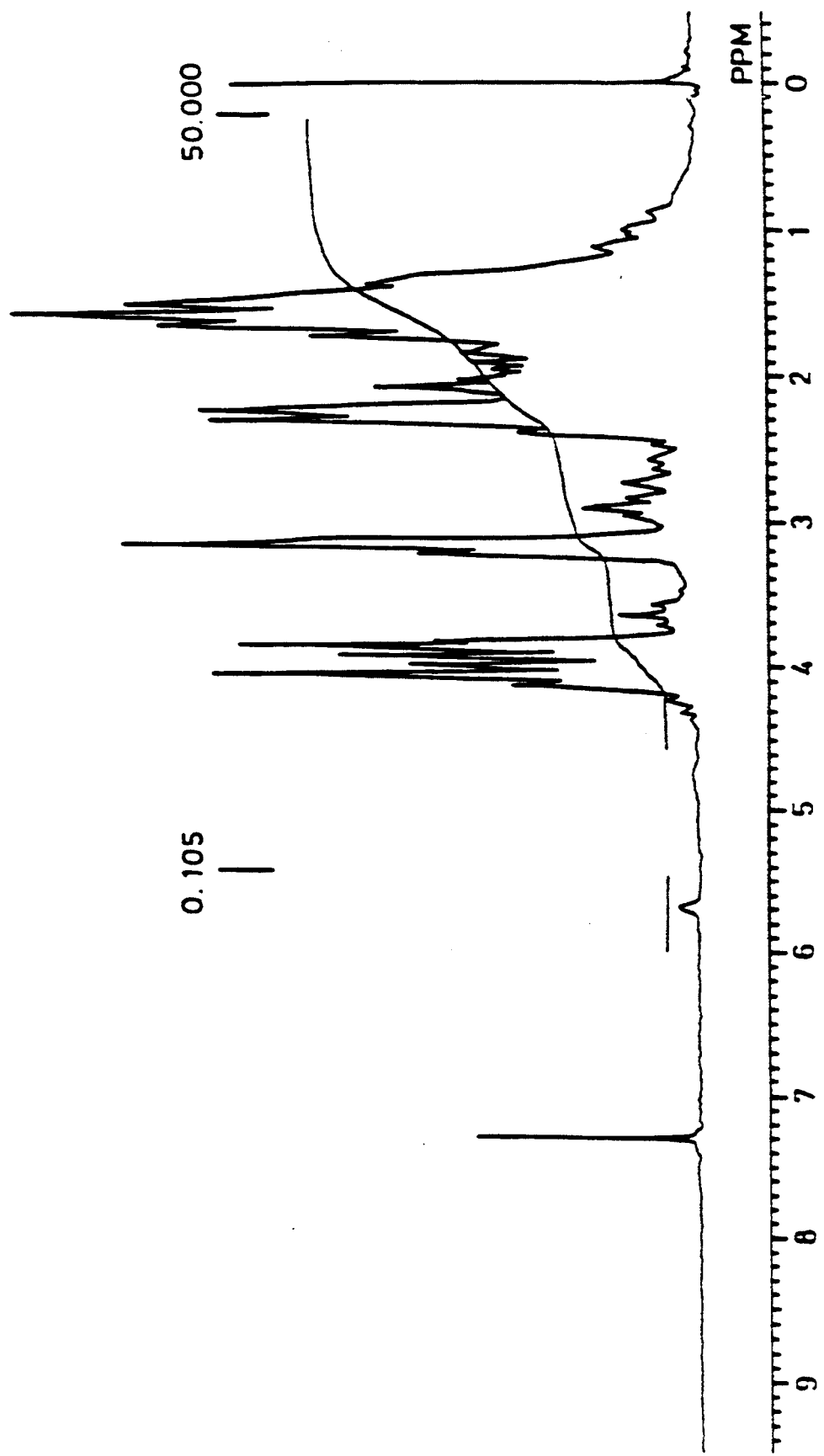
FIG. 25 is $^1$H-NMR chart.

In the IR spectrum chart(FIG. 25), an absorption peak was observed at 1,723 cm$^{-1}$, which is derived from carbonyl group, absorption peaks were observed at 1,249 cm$^{-1}$, 896 cm$^{-1}$ and 783 cm$^{-1}$, which are derived from an epoxy ring.

Figure 26:
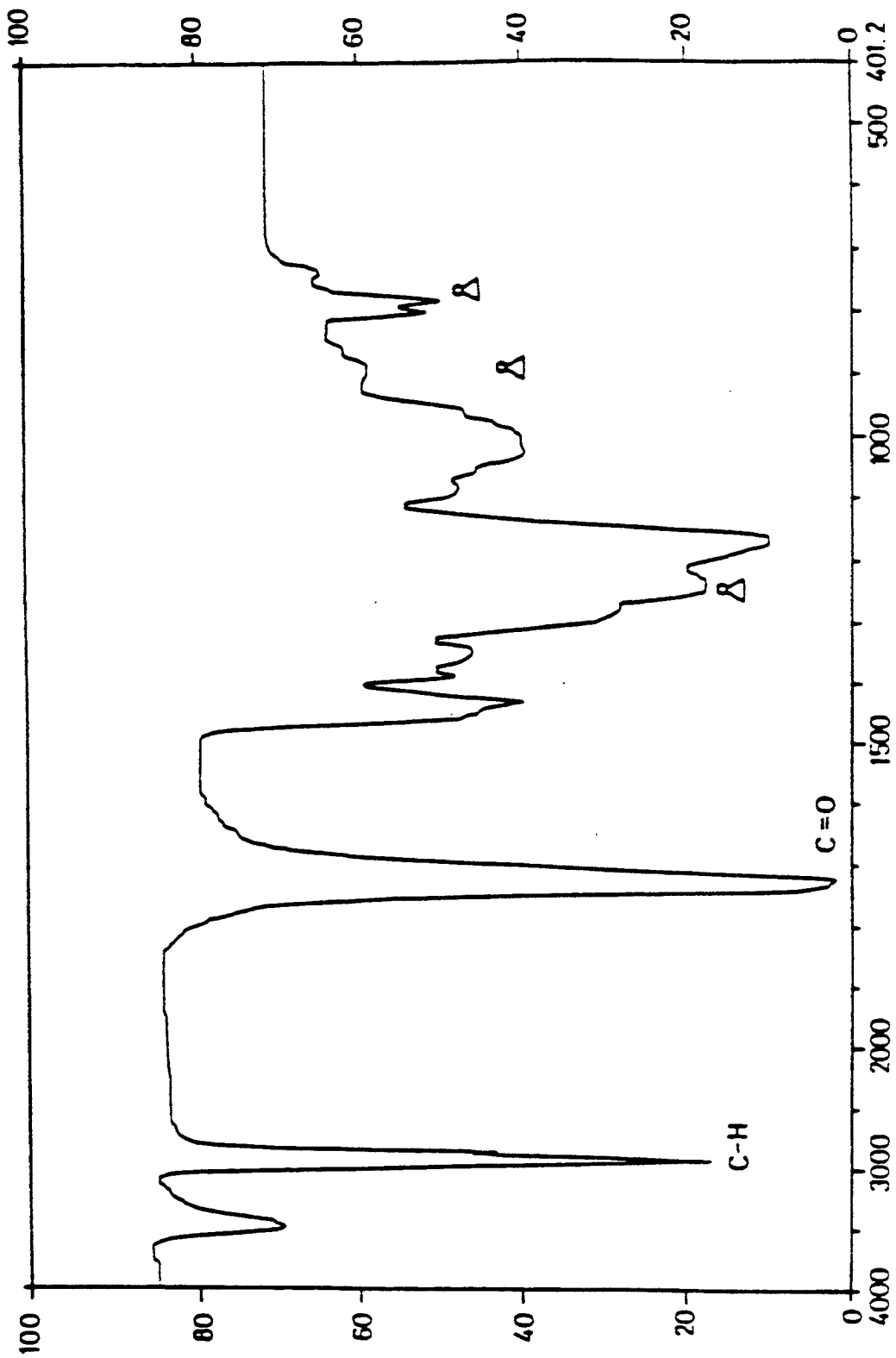
FIG. 26 is an IR spectrum chart and FIG. 27 is a GPC chart relating to a composition obtained in Example 13, respectively.
Figure 27:
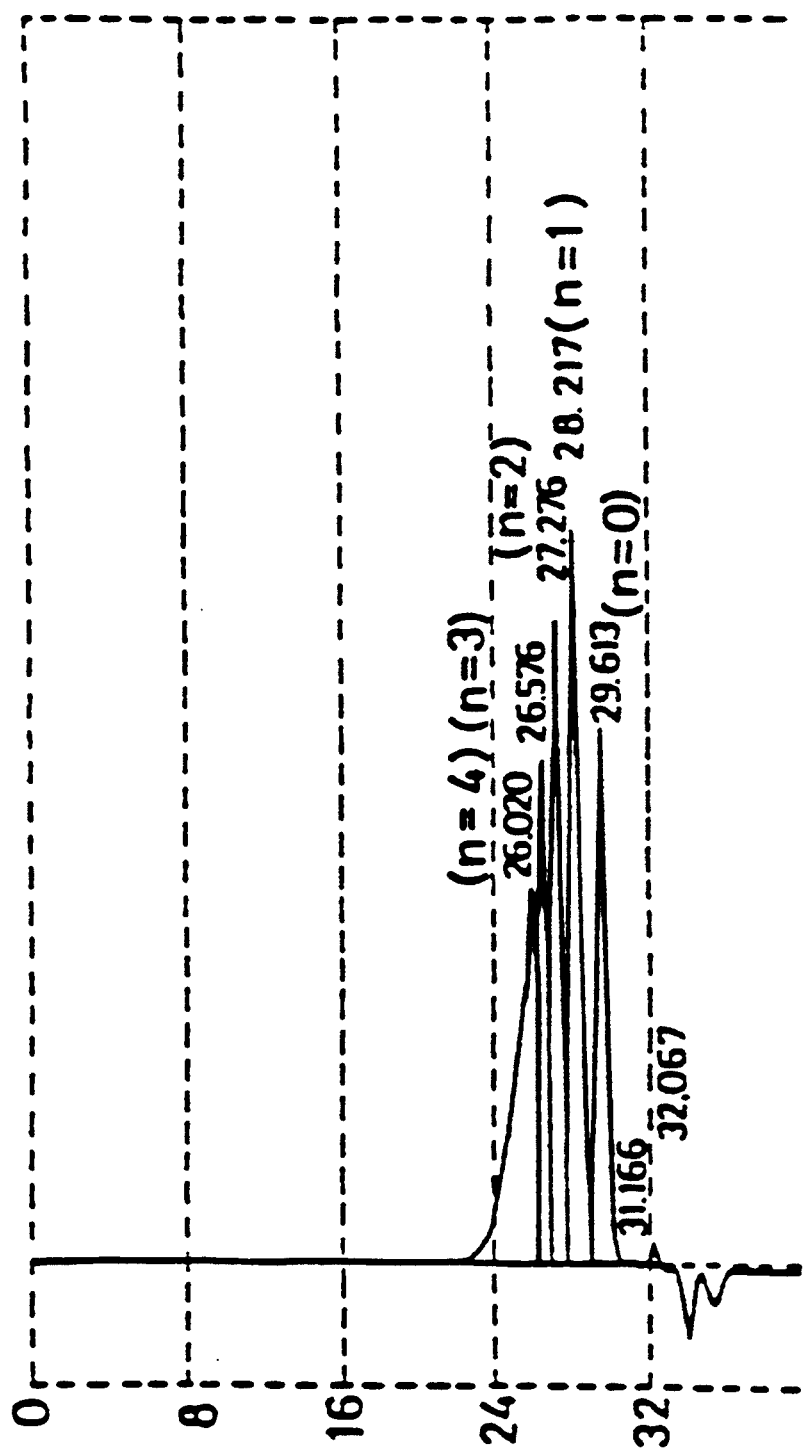

Furthermore, the GPC chart (FIG. 26) illustrates that the product is a mixture composed of a compound into which no epsilon-caprolactone derived ester-bonding unit is introduced(n=0), a compound into which one mol of epsilon-caprolactone derived ester-bonding unit is introduced(n=1), and compounds which have a distribution(n=2,3,4, ... ) of more than 1 mol of epsilon-caprolactone derived ester-bonding unit.

It was confirmed that the product is represented by the general formula described hereinafter by the above analyses;

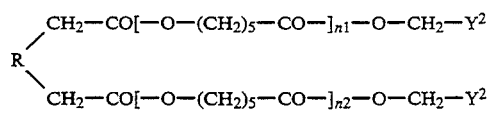

[wherein $Y^2$ represents

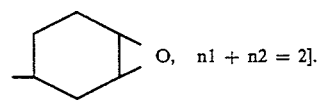

O,  n1 + n2 = 2].

The epoxide composition obtained was designated as EP-1.

EXAMPLE 14

A reaction vessel equipped with a stirrer, a tube for distilling water was charged with 468.3 g. of 1,2,3,4-butanetetracarboxylic acid, 1,100 g. of 3-cyclohexene 1-methanol and 684.8 g. of epsilon-caprolactone.

The contents in the vessel were gradually raised to a temperature of 150° C. over 2 hours, as a result, the contents became homogeneous, followed by initiation of water distillation.

Additionally, the reaction temperature was raised to 220° C. over approximately 3 hours, and further reaction was continued for approximately 45 hours while removing water.

Subsequently, the contents were cooled to a temperature of 140° C., and then excessively charged 3-cyclohexene 1-methanol was distilled out of the reaction system over approximately 3 hours over a reduced pressure of 1 to 10 mm Hg, to obtain 2,050 g. of a liquid product. It was confirmed that by gas chromatography analysis the less than 0.1% of unreacted 3-cyclohexene 1-methanol remained in the product.

Subsequently, the product obtained was analyzed with a GPC equipment, a $^1$H-NMR equipment and an IR spectrometer to obtain the same structures as the product obtained in Example 2.

EXAMPLE 15

The same procedures described as in Example 14 were repeated, except that 228.3 g. of epsilon-caprolactone was used to obtain 1,593.3 g. of a liquid product.

It was confirmed that by gas chromatography analysis the less than 0.1% of unreacted 3-cyclohexene 1-methanol remained in the product. Successively, the product obtained was analyzed with a GPC equipment, a $^1$H-NMR equipment and an IR spectrometer to obtain the same structures as the product obtained in Example 1.

EXAMPLE 16

A reaction vessel equipped with a stirrer and a tube for distilling water was charged with 1,521 g. of 1,2,3,4-butanetetracarboxylic acid, 2,293 g. of 3-cyclohexene 1-methanol and 1,140 g. of epsilon-caprolactone.

The contents in the reaction vessel were gradually raised to a temperature of 150° C. over 2 hour, as a result, the contents became roughly homogeneous, then water distillation was started.

Additionally, the reaction temperature was raised to 220° C. over approximately 3 hours, and further reaction was continued for approximately 50 hours.

Successively, the contents were cooled to a temperature of 140° C., and then excess 3-cyclohexene 1-methanol charged was distilled out of the reaction system for approximately 3 hours under a reduced pressure of 1 to 10 mm Hg, to obtain 2,050 g. of a liquid product. It was confirmed that less than 0. 1% of 3-cyclohexene 1-methanol remained in the product obtained, as a result of gas chromatography analysis.

Successively, the product obtained was analyzed with a $^1$H-NMR equipment and an IR spectrometer to confirm the same structure as obtained in Example 10.

EXAMPLE 17

The same procedures described as in Example 11 were repeated, except that 1,040 g. of 1,2,3,4-butanetetracarboxylic acid, 1,550 g. of 3-cyclohexene 1-methanol and 1,520 g. of epsilon-caprolactone was used.

Subsequently, the product obtained was analyzed with a $^1$H-NMR equipment and an IR spectrometer to confirm the same structure as obtained in Example 11.

Application Example 1

100 parts by weight of the obtained epoxide EP-1 [the present composition which comprises a compound represented by the formula(II)] in Example 13 and 3 parts by weight of Degacure K126(a photo-cationic polymerization initiator manufactured by Degussa AG, Germany) were mixed and cured to obtain a cured plate having a thickness of 2 mm under the illumination of an irradiation with a metalhalide lamp having 80 W/cm, with the exposing distance of 6.5 cm, for the period of time of 100 seconds.

Comparative Application Example 1.

The same procedures as described in Application Example 1 were repeated, except that 100 parts by weight of 3,4-epoxycyclohexylmethyl-3',4'-epoxycyclohexanecarboxylate [Celloxide 2021 manufactured by Daicel Chemical Industries, Ltd., which is a conventional alicyclic epoxy resin not having any lactone units] were used to obtain a cured plate.

Comparative Application Example 2

The same procedures as described in Application Example 1 were repeated, except that 100 parts by weight of Epikote 828 [an epi-bis type epoxy resin manufactured by Ciba-Geigy, Corp.] and catalysts described in Table 1 were used to obtain a cured plate.

The measurements of the properties of the cured plates were carried out under the conditions of temperature of 20° C. and relative humidity of 65%. Measurements of the tensile strength and elongation were carried out based on JIS K 6911.

The measurements of Tg. were carried out with a high performance differential calorimeter (No. DSC 8230B manufactured by Rigaku Denki, Ltd.).

The mixing constituents and various properties obtained in Application Example 1 and Comparative Application Examples 1, 2 are shown in Table 1.

EXAMPLE 18

A 5-necked reaction vessel equipped with a stirrer and a tube for supplying air, a thermometer, a reflux condenser and a funnel for dropwise addition was charged with 507 parts by weight of the epoxide obtained [the present composition which comprises a compound represented by the formula(II)] in Example 12 and 0.44 parts by weight of hydroquinone monomethyl ether(as a polymerization inhibitor).

Successively, a mixture of 144 parts by weight of acrylic acid(as an unsaturated organic compound) and 0.70 parts by weight of triethylamine(as a catalyst) was supplied by dropwise addition while maintaining at a temperature range of 80° to 90° C., and supplying air over approximately 2 hours.

The reaction was continued for approximately 24 hours after completion of the dropwise addition to obtain the present photo-cationically polymerizable vinyl composition having properties of acid value of 1.20 mg KOH/g, an oxirane oxygen of 2.18% and a viscosity of 300,000 cp/25° C.

The composition obtained was designated as EA-1.

EXAMPLE 19

The same procedures as described in Example 18 yore repeated, except that 536 parts by weight of the epoxidized composition [the present composition which comprises a compound represented by the formula (II)] obtained in Example 7, 0.44 part by weight of hydroguinone monomethyl ether(as a polymerization inhibitor) and 0.70 part by weight of triethylamine were used to obtain the present photo-cationically polymerizable vinyl composition having properties of acid value of 4.35 mg KOH/g, an oxirane oxygen of 0.12% and a viscosity of 2,000,000 cp/25° C.

The composition obtained was designated as EA-2:

Comparative Example 1

A 5-necked reaction vessel equipped with a stirrer and a tube for supplying air, a thermometer, a reflux condenser and a funnel for dropwise addition was charged with 930 parts by weight of Araldite 6071 (an epi-bis type epoxy resin having an epoxy equivalent of from 450 to 500, not having any lactone derived ester-bonding units, manufactured by Ciba-Geigy, Corp.) and 0.54 part by weight of hydroquinone monomethyl ether.

Successively, a mixture of 144 parts by weight of acrylic acid and 1.07 parts by weight of triethylamine as a catalyst was supplied by dropwise addition while keeping at a temperature range of 80° to 90° C., and supplying air over approximately 2 hours.

The reaction was further continued for 24 hours after completion of the dropwise addition to obtain a polymerizable compound having an acid value of 3.38 mg KOH/g, oxirane oxygen of 0.09% and a viscosity of 2,000,000 cp/25° C.

Application Example 2

50 parts by weight of the compositions obtained in Example 18 and 19, 20 parts by weight of trimethylolpropane triacrylate, 20 parts by weight of 1,6-hexane diol diacrylate, 10 parts by weight of N-vinylpyloridone, 2 parts by weight of benzoin isobutylether as a photo-initiator and 2 parts by weight of benzylmethyl ketal were mixed to obtain the present photo-curable composition.

The photo-curable compositions obtained in Examples 18 and 19 were coated on a iron substrate to form a coating layer having a thickness of 15 microns, respectively.

Successively, the coated layers were cured with irradiation by a high-voltage mercury lamp having an radiation power of 80 W/cm², maintaining a distance of 10 cm under the illuminance of an irradiation, with a moving speed of 2 m/min.

Application Example 3

50 parts by weight of the compositions obtained in Example 19, 20 parts by weight of trimethylolpropane triacrylate, 20 parts by weight of 1,6-hexane diol diacrylate, 10 parts by weight of N-vinylpyloridone, 2 parts by weight of benzoin isobutylether as a photo-initiator and 2 parts by weight of benzylmethyl ketal were mixed to obtain the present photo-curable composition.

The photo-curable compositions obtained were coated on a iron substrate to form a coating layer having a thickness of 15 microns, respectively.

Successively, the coated layers were cured with irradiation by a high-voltage mercury lamp having an radiation power of 80 W/cm², maintaining a distance of 10 cm under the illuminance of an irradiation, with a moving speed of 2 m/min.

Comparative Application Example 3

The same procedures as described in Application Example 1 were repeated, except that 50 parts by weight of the polymerizable compound obtained in Comparative Example 3 was used to obtain a photo-curable composition.

The photo-curable composition obtained was coated on a iron substrate to form a coating layer having a thickness of 15 microns.

Successively, the coated layers were cured as described in Application Example 2.

The mixing constituents and results obtained in Application Examples 2, 3 and Comparative Application Example 3 are shown in Table 2.

As described in the Table 2, the photo-cured coating layers prepared with the present photo-curable composition have excellent bending resistance as compared with conventional one.

While the invention has been described in detail and with reference to specific embodiments thereof, it will be apparent to one skilled in the art that various changes and modifications can be made therein without departing from a spirit and scope thereof.

TABLE 1

|  | Application Example 1 | Comparative Application Example 1 | Comparative Application Example 2 |
|---|---|---|---|
| EP-1 | 100 | | |
| Celloxide 2021(*1) | | 100 | |
| Epikote 828(*2) | | | 100 |
| TAAA(*3) | 0.5 | 0.5 | |
| TEAACA(*4) | | | 0.5 |
| TPONBS(*5) | 3 | 3 | |
| TBDPS(*6) | | | 3 |
| Glass transition Temperature (°C./DSC) | −23 | 160 | * |
| Tensile strength (kgf/mm2) | 0.3 | 4.2 | * |
| Tensile elongation (%) | 160 | 4 | * |

Note:
Celloxide 2021: 3,4-epoxycycrohexylmethyl-3',4'-epoxycyclohexanecarboxylate [manufactured by Daicel Chemical Industries, Ltd.]
Epikote 828: epi-bis type epoxy resin [manufactured by Ciba-Geigy, Corp.]
TAAA: trisacetylacetonato aluminum
TEAACA: trisethylacetoacetato aluminum
TPONBS: triphenyl(o-nitrobenzyloxy)silane
TBDTS: t-butyldiphenyl(5-methyl-2-nitrobenzyloxy)silane
*incapable of measuring because of no-curing

TABLE 2

|  | Application Example 2 | Application Example 3 | Comparative Application Example 2 |
|---|---|---|---|
| EA-1 | 50 | | |
| EA-2 | | 50 | |
| Epoxy Acrylate made from Araldite 6071(*1) | | | 50 |
| TMPTA(*2) | 20 | 20 | 20 |
| HDDA(*3) | 20 | 20 | 20 |
| DPEHA(*4) | | | |
| NVP(*5) | 10 | 10 | 10 |
| BIBE(*) | 2 | 2 | 2 |
| BDMK(*7) | 2 | 2 | 2 |
| surface hardness (pencil) | 211 | 211 | 211 |
| clinging ability | excellent | excellent | excellent |
| flexural resistance | excellent | excellent | poor |

Note:
Araldite 6071: epi-bis type epoxy resin [manufactured by Ciba-Geigy, Corp.]
TMPTA: trimethylolpropane triacrylate
HDDA: 1,6-hexanadiol diacrylate
DPEHA: dipentaerythrytolhexaacrylate
NVP: N-vinyl pyrrolidone
BIBE: benzoin isobutylether (photoinitiator)
BDMK: benzyl dimethyl ketal(Irugacure 651 manufactured by Ciba-Geigy Corp.)

What is claimed is:

1. A lactone-modified alicyclic compound of the formula

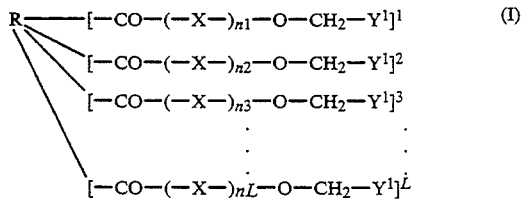

wherein, R is an alkyl group, an aromatic group or an alkenyl group having carbon number of from 1 to 30, $Y^1$ is at least one of the structural groups;

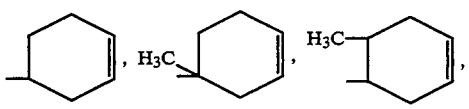 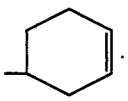

X is the structural group derived from a lactone

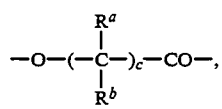

$R^a$ and $R^b$ each independently is hydrogen or a methyl group, c is a number of from 4 to 8, n1 to nL represents 0 or a number of more than 0, respectively, $n1+n2+n3+ \ldots +nL$ is 1 or a number of more than 1, which corresponds to the total mole number of lactone introduced into one molecule, L represents 2 or a number of more than 2.

2. A compound as set forth in claim 1, wherein said X is —O—(CH$_2$)—CO—.

3. A compound as set forth in claim 1, wherein said $Y^1$ is

4. A compound as set forth in any one of claims 1 to 3, wherein said R is

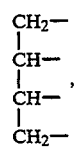

5. A compound as set forth in any one of claims 1 to 3, wherein said R is

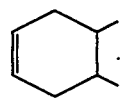

* * * * *